United States Patent
Zeng et al.

(10) Patent No.: US 10,682,078 B2
(45) Date of Patent: Jun. 16, 2020

(54) APPARATUS AND METHODS FOR MATCHING OF TINNITUS

(71) Applicant: The Regents Of The University Of California, Oakland, CA (US)

(72) Inventors: Fan-Gang Zeng, Irvine, CA (US); Duo Zhang, Oakland, CA (US); Janice Erica Chang, Irvine, CA (US)

(73) Assignee: The Regents Of The University Of California, Oakland, CA (US)

( * ) Notice: Subject to any disclaimer, the term of this patent is extended or adjusted under 35 U.S.C. 154(b) by 443 days.

(21) Appl. No.: 14/211,642

(22) Filed: Mar. 14, 2014

(65) Prior Publication Data

US 2015/0073296 A1    Mar. 12, 2015

Related U.S. Application Data

(60) Provisional application No. 61/782,208, filed on Mar. 14, 2013.

(51) Int. Cl.
*A61B 5/12* (2006.01)
*A61B 5/00* (2006.01)

(52) U.S. Cl.
CPC .............. *A61B 5/128* (2013.01); *A61B 5/123* (2013.01); *A61B 5/7435* (2013.01); *A61B 5/7475* (2013.01)

(58) Field of Classification Search
CPC ....... A61M 21/00; H04R 25/75; A61N 1/361; A61B 5/128; A61F 11/00
See application file for complete search history.

(56) References Cited

U.S. PATENT DOCUMENTS

| 8,357,102 | B2 | 1/2013 | Zeng et al. | |
| 8,795,193 | B2 | 8/2014 | Zeng et al. | |
| 2007/0093733 | A1* | 4/2007 | Choy | A61F 11/00 601/84 |
| 2010/0016755 | A1* | 1/2010 | Henry | A61B 5/7435 600/559 |
| 2011/0105967 | A1* | 5/2011 | Zeng | A61M 21/00 601/47 |
| 2012/0283593 | A1* | 11/2012 | Searchfield | A61M 21/00 600/559 |

* cited by examiner

*Primary Examiner* — Patrick Fernandes
(74) *Attorney, Agent, or Firm* — Gordon & Rees LLP

(57) ABSTRACT

Apparatuses and methods for matching the tinnitus of a subject are provided. A plurality of sounds are applied to a subject. The plurality of sounds includes a plurality of first sounds and further includes a plurality of second sounds. A first likeness score associated with the plurality of the sounds is received. Each first likeness score is representative of the similarity of the sound associated therewith to the tinnitus of the subject. At least one third sound is generated based on at least one of the plurality of first sounds and based on at least one of the plurality of second sounds. The at least one third sound is generated based on the first likeness scores associated with the plurality of sounds. A fourth sound is determined based on the at least one third sound. The fourth sound matches the tinnitus of the subject.

18 Claims, 23 Drawing Sheets

APPARATUS AND METHODS FOR MATCHING OF TINNITUS

CROSS-REFERENCE TO RELATED APPLICATION

This application claims priority to U.S. Provisional Application No. 61/782,208 titled "APPARATUS AND METHODS FOR MATCHING OF TINNITUS", filed Mar. 14, 2013, the entire disclosure if which is incorporated by reference herein in its entirety.

BACKGROUND

Tinnitus, a common auditory disorder, is most commonly known as "ringing of the ears" but is generally the perception of any type of sound in the absence of an external source of sound. Worldwide, tinnitus has been estimated to affect 10-15% of the population. Recent studies estimate the prevalence of tinnitus in the United States at 25.3%, affecting an estimated 50 million Americans (Shargorodsky et al., 2010). There currently is no cure, nor is there a standardized method to characterize tinnitus. Despite early attempts to characterize tinnitus dating back to the early 1900s (Snow, 2004) and a formalized call by the CIBA foundation in 1981 to develop general guidelines for the clinical assessment of tinnitus (Evered and Lawrenson, 1981), clinical tinnitus matching procedures have yet to be standardized and universally adopted in the current day (Henry and Meikle, 2000; Tyler, 2000; Henry et al., 2001; 2004). Although efforts have been made to find neural correlates of tinnitus, an objective measure of tinnitus does not yet exist (Miihlnickel et al., 1998; Diesch et al., 2010; Zeng et al., 2011a). Hence most current strategies focus on psychophysical methods. This is a critical procedure as the first step after a patient presents to a clinic with tinnitus is a medical evaluation from an otolaryngologist and audiologic assessment from an audiologist.

Yet there exists much room for improvement in psychophysical characterization of a patient's tinnitus percept. A paramount challenge of tinnitus matching is the sheer heterogeneity of the tinnitus percept experienced by tinnitus patients. Nearly half (46%) of patients have complex tinnitus consisting of more than one type of sound (Meikle et al., 1995). A questionnaire study characterizing tinnitus asked 528 patients to identify the sound quality most descriptive of their tinnitus. Common descriptors included ringing (38%), buzzing (11%), crickets (9%), along with hissing (8%), whistling (7%), humming (5%), and more (Stouffer and Tyler, 1990). It is against this observation of the heterogeneity of the tinnitus percept that the apparatuses and methods for matching tinnitus described herein were developed.

SUMMARY

Apparatuses and methods for matching of tinnitus are described herein. In some embodiments, a method for matching tinnitus in a human subject includes applying a plurality of sounds to a subject. The plurality of sounds comprising a plurality of first sounds and further comprising a plurality of second sounds. The method also includes receiving a first likeness score associated with the plurality of the sounds. Each first likeness score is representative of the similarity of the sound associated therewith to the tinnitus of the subject. The method also includes generating at least one third sound based on at least one of the plurality of first sounds and based on at least one of the plurality of second sounds. The generating is based on the first likeness scores associated with the plurality of sounds. The method additionally includes determining a fourth sound based on the at least one third sound, wherein the fourth sound matches the tinnitus of the subject.

In some embodiments, a method for matching tinnitus in a human subject includes applying a sound to a subject and receiving from the subject, in response to the applying, a specification of a perceived loudness and a specification of one or more perceived cut-off frequencies of a band-pass noise. The perceived loudness corresponds to the loudness of the tinnitus of the subject, and the perceived cut-off frequencies correspond to an upper cut-off frequency of the tinnitus of the subject, or to a lower cut-off frequency of the tinnitus of the subject, or both. The method further includes determining a center frequency and a frequency bandwidth based on the perceived cut-off frequencies. The method also includes generating a second sound that matches the tinnitus of the subject based on the perceived loudness, the center frequency and the frequency bandwidth.

In some embodiments, an apparatus for matching tinnitus in a human subject includes an audio interface module configured to apply a plurality of sounds to a subject. The plurality of sounds comprises a plurality of first sounds and further comprising a plurality of second sounds. The apparatus also includes an input module configured to receive a first likeness score associated with the plurality of the sounds. Each first likeness score is representative of the similarity of the sound associated therewith to the tinnitus of the subject. The apparatus also includes an audio generation module comprising a sound generator, responsive to the likeness scores associated with the plurality of sounds, configured to generate at least one third sound based on at least one of the plurality of first sounds and based on at least one of the plurality of second sounds. The generating is based on the first likeness scores associated with the plurality of sounds. The apparatus also includes an analysis module, responsive to an input signal from the subject, to determine a fourth sound based on the at least one third sound, where the fourth sound matches the tinnitus of the subject. At least one of the audio interface module, the input module, and the audio generation module is implemented in one or more of a memory and a processing device.

In some embodiments, an apparatus for matching tinnitus in a human subject includes an audio interface module configured to apply a sound to a subject and an input module configured to receive, in response to the applying, a signal indicative of a perceived loudness and a signal identifying one or more perceived cut-off frequencies. The perceived loudness corresponds to the loudness of the tinnitus of the subject and the perceived cut-off frequencies correspond to an upper cut-off frequency of the tinnitus of the subject, or of a lower cut-off frequency of the tinnitus of the subject, or both. The apparatus also includes a memory constructed to store data corresponding to a characteristic frequency and a bandwidth based on the perceived cut-off frequencies. The apparatus also includes an audio generation module comprising a sound generator to generate a second sound corresponding to the tinnitus of the subject based on the perceived loudness, the characteristic frequency and the frequency bandwidth. At least one of the audio interface module, the input module, and the audio generation module is implemented on one or more of the memory and a processing device.

DETAILED DESCRIPTION

Figure 1:
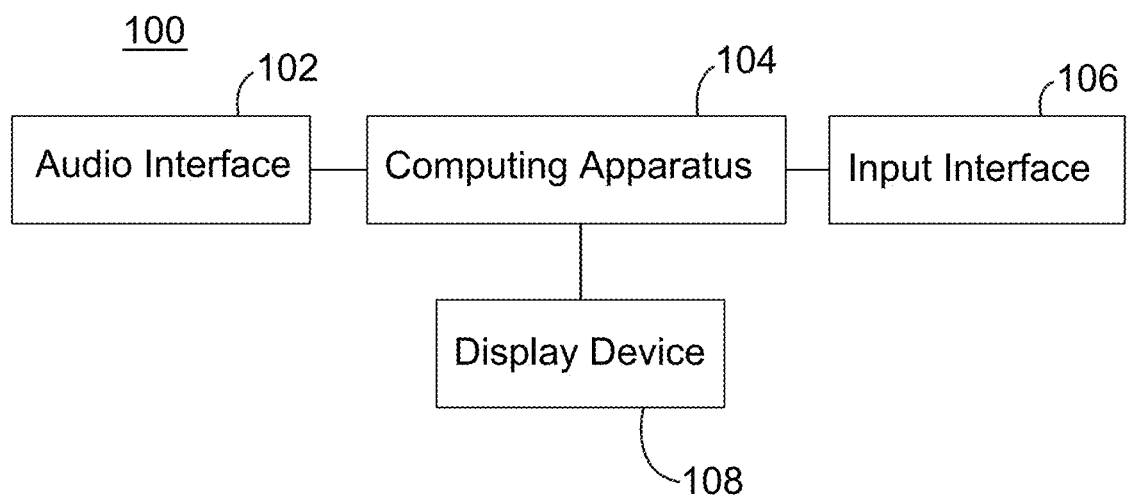
FIG. 1 is an illustration of a system of the invention, according to an embodiment.

Generally, embodiments disclosed herein are operable for matching the tinnitus of a human subject. Particularly, embodiments disclosed herein are operable to perform this function by generating one or more sounds that can effectively mask the tinnitus of the subject, and applying the generated sound(s) to the patient.

As used in this specification, the singular forms "a," "an" and "the" include plural referents unless the context clearly dictates otherwise. Thus, for example, the term "a device" is intended to mean a single device or a combination of devices.

Apparatus, and methods for matching the tinnitus of a human subject are described herein. In some embodiments, one or more sounds is applied to the subject. The applied sound(s) can be characterized in any suitable manner, such as having a specified loudness, center frequency, bandwidth, SNR, and/or the like. Generally, it is understood that, unless explicitly characterized otherwise, the various sounds disclosed herein can each independently include or consist of one or more of the following: a single frequency component, multiple frequency components, a pure tone, one or more harmonics, a white noise, and/or the like.

In some embodiments, the applied sound(s) is generated using a specification of such sound characteristics. In some embodiments, the applied sound(s) can be designed using a reference, such as other tinnitus patients, for example.

The applied sound(s) can be delivered to the subject via any suitable audio interface/device, such as speakers, headphones, hearing aids and/or the like. In some embodiments, a mechanical equivalent of the applied sound(s) is delivered to the subject, such as via a bone-conduction device; in other embodiments, an electrical equivalent of the applied sound(s) is delivered to the subject, via a cochlear implant and/or brainstem implant.

In some embodiments, the applied sound(s) is based on user input received when one or more tinnitus matching procedures are presented to the subject, where the user input can include a selection of a tinnitus matching procedure.

For example, a subject can select a first procedure, and the applied sound(s) can include a plurality of sounds sequentially applied to the subject. In some embodiments, each of the plurality of sounds can be distinct. In some embodiments, the plurality of sounds can be a plurality of pure tones having a different center frequency that is equidistant from the center frequency of a succeeding/preceding pure tone. For example, in some embodiments, the plurality of sounds can have a center frequency ranging from 500 Hz for a first sound to 16 kHz for a last sound in half-octave steps.

In some embodiments, user input is associated with the hearing threshold of the subject. Accordingly, in some embodiments, each sound (e.g. a pure tone) can be presented in the following manner: the sound is initially presented at a low/sub-threshold level, and the level can be increased stepwise (e.g. by 5 dB) until the subject responds to indicate that the applied sound is perceptible at a first response level. In some embodiments, the sound level is increased by a predetermined amount (e.g. by 10 dB) and then again decreased (e.g. by 5 dB) until the subject indicates that the applied sound is imperceptible, to yield a second response level. The first and second response level can then be averaged, so as to avoid "overshoot and undershoot" effects, for example. In this manner, the subject's hearing threshold can be more accurately determined.

In some embodiments, the first procedure can further include determining a loudness of the tinnitus of the subject based on the applied sounds. In some embodiments, user input associated with the loudness of the applied sounds, as matched to the subject's tinnitus can be received. For example, in some embodiments, the subject can be asked to adjust the sound level of each sound of the plurality of sounds having a center frequency ranging from 500 Hz for a first sound to 16 kHz for a last sound in half-octave steps. In some embodiments, for each sound, one or more of the user inputs is received: an indication when the applied sound is just noticeably louder than the subject's tinnitus; when the applied sound is just noticeably softer than the subject's tinnitus; and when the applied sound has equal loudness to the subject's tinnitus. In some embodiments, the loudness level for an applied sound is determined by averaging these user inputs as an estimate of the tinnitus loudness.

In some embodiments, the first procedure can further include determining the similarity and/or the "likeness" of the applied sound to the tinnitus of the subject. In some embodiments, the likeness can be determined by applying a plurality of loudness-matched sounds to the subject. A loudness matched sound can be one that has a loudness most similar to a loudness of a similar sound (i.e. have similar frequency component(s)) as employed for the loudness determination described above. In some embodiments, the plurality of sounds can include a plurality of first sounds and a plurality of second sounds. In some embodiments, the plurality of first sounds can be loudness-matched (as described above) pure tones, each having a distinct center frequency. In some embodiments, the plurality of second sounds can be loudness-matched band noises, each having a distinct center frequency and a distinct bandwidth. In some embodiments, the plurality of second sounds can include a white noise, i.e., a sound with a flat/constant power spectral density. In some embodiments, at least one of the plurality of sounds can be presented multiple times. In some embodiments, the subject can verify that the loudness matched sound(s) is indeed similar in loudness to his tinnitus, which can be instantaneously adjusted by the subject and/or automatically based on the verification.

In some embodiments, the subject provides an indication of likeness and/or similarity for each of the plurality of sounds (i.e. for each of the first sounds and for each of the second sounds) as compared to his tinnitus. The likeness can be indicated by the user in any suitable manner including, but not limited to, a likeness score for each of the plurality of sounds, a percentage match for each of the plurality of sounds, a ranking of the plurality of sounds, a selection/rejection classification for each of the plurality of sounds, a setting on an analog and/or digital slider with the extremes of the slider representing similarity/dissimilarity, and/or the like. In this manner, a subject can provide an indication of a center frequency as well as a noise band that best matches his tinnitus.

In some embodiments, likeness determination results in a selection of one of the first sounds having the most likeness (e.g. likeness score, used hereon for simplicity of explanation) of all the first sounds, and of one of the second sounds having the highest likeness score of all second sounds. In some embodiments, the subject is asked to verify his hearing threshold and/or loudness level, determined as described earlier, for at least one of the selected first sound and the selected second sound.

In some embodiments, the first procedure can further include generating one or more third sounds from the selected first sound and the selected second sound. In some embodiments, the one or more third sounds has sound characteristics based on one of the first sounds having the highest likeness score of all first sounds, and one of the second sounds having the highest likeness score of all second sounds. In some embodiments, at least one third sound is generated by mixing the selected first sound and the selected second sound. In some embodiments, a plurality of third sounds are generated by mixing the selected first sound and the selected second sound, where each third sound has a different ratio of the selected first sound to the selected second sound. In other words, when the first sounds are associated with pure tones and the second sounds are associated with noise, each third sound of the plurality of third sound can have a distinct signal-to-noise ratio (SNR). In some embodiments, the SNR can be selected from 0, ±5, ±10, ±15, ±20, ±25, ±30, ±35, ±40, ±Inf, and all values in between.

In some embodiments, the first procedure can further include presenting the plurality of third sounds to the subject, and receiving a determination of likeness (e.g. a likeness score used hereon for simplicity of explanation) for each third sound indicating the likeness of the third sound to the tinnitus of the subject.

In some embodiments, the first procedure can further include determining a fourth sound based on the plurality of third sounds that best matches the tinnitus of the subject. In some embodiments, the fourth sound is a selected third sound having the highest likeness score as determined above. In some embodiments, the fourth sound is based on the selected third sound after one or more processing steps. For example, in some embodiments, an octave verification step is performed using the selected third sound in the following manner: the selected third sound can be used to generate at least two additional sounds, where a first additional sound is one octave lower than the selected third sound and a second additional sound is one octave higher than the selected third sound. In some embodiments, the subject is asked to choose between the selected third sound and the two additional sounds in any suitable manner, such as by likeness determination for example. The fourth sound can then based on the chosen sound of the subject. In some embodiments, the subject is asked to choose by playing the selected third sound and the two additional sounds in pairs in a random order, and asking the subject to make a forced judgment (e.g. a two-alternative forced choice (2AFC) judgment) for one sound in each pair. The fourth sound can then be based on the forced judgments made by the subject.

In some embodiments, the first procedure can further include determining the fourth sound based on a sound vector associated with the selected third sound. In some embodiments, the sound vector is based on sound characteristics of the selected third sound, and can include, but is not limited to, one or more of a center frequency, a bandwidth, a pure tone-to-noise ratio, a loudness, and a threshold. In other words, the sound vector can be an N-dimensional vector, with each dimension associated with a sound characteristic, and can represent the subject's tinnitus. In some embodiments, the sound vector can be used as input to search an N-dimensional space, and/or a subset thereof, of candidate sounds to predict, match, and/or otherwise determine a candidate sound that would best match (and thereby cure) the subject's tinnitus. For example, a candidate sound may be determined that has one or more sound characteristics within a specified threshold of that specified in the sound vector. As another example, results of previous searches can be 'learned' from for determining the best search strategy, such as by selecting and searching a subset of the N-dimensional space. In this manner, embodiments described herein are operable in scenarios where pre-engineered sounds are selected based on independent matching of the subject's tinnitus. The fourth sound can then be applied to the subject (e.g. via the audio interface/device), thereby suppressing the tinnitus of the subject.

Hence, as disclosed herein, the first procedure is operable to generate the fourth sound based on user input, that in turn is based on the user's perception of the sound. In some embodiments, other procedure(s) can be employed that permit the subject to directly manipulate the sound characteristics of an applied/presented/generated sound. Accordingly, in some embodiments, a second procedure is selectable by the subject that applies a single sound to the subject which can be determined and/or designed in a manner similar to the applied sound(s) of the first procedure. In response, the subject can directly modulate the loudness of the single sound to match his tinnitus; in other words, by virtue of such modulation, the subject can specify a perceived loudness of his tinnitus. In this manner, rather than playing different sounds at different levels sequentially and asking the subject to pick the best match, a subject can quickly reach a consensus on what is the best match for his tinnitus. The subject can module the loudness, and thereby indicate a perceived loudness of his tinnitus, via any suitable audio and/or visual input means, including, but not limited to, a rotary selector, a volume control, a drop-down menu, a sliding scale, and/or the like.

In some embodiments, the second procedure can also include receiving, from the subject, a specification of one or more perceived cut-off frequencies of a band-pass noise of the subject's tinnitus. In other words, in a manner similar to that described above, the subject can be allowed to modulate an upper cutoff frequency and/or a lower cutoff frequency of the single sound until he perceives that it matches the noise in his tinnitus. In some embodiments, a sliding scale can be employed (see FIG. 7).

In some embodiments, a center frequency and/or bandwidth can be determined from the cut-off frequencies. For example, in some embodiments, the center frequency can be the average of the specified upper cutoff frequency and the specified lower cutoff frequency. In some embodiments, the bandwidth can be the difference between the specified upper cutoff frequency and the specified lower cutoff frequency. In some embodiments, the bandwidth can be determined to be zero (i.e. the subject is indicating his tinnitus has no noise component) if the difference between the specified upper cutoff frequency and the specified lower cutoff frequency is within a specified threshold.

In some embodiments, the second procedure can also include generating a second sound based on the determined center frequency, and based on the determined bandwidth, if any. In some embodiments, the second sound has sound characteristics that include the determined center frequency and the determined bandwidth. In some embodiments, octave verification (described earlier) can be performed on a sound based on the determined center frequency and the determined bandwidth, and the second sound can be based on the result of the octave verification. In some embodiments, the second sound can be based on a likeness score received from the subject for any sound generated based on the determined center frequency and the determined bandwidth. In some embodiments, only if the likeness score meets a predetermined threshold is the generated sound used as the basis for the second sound.

Some embodiments described herein, permit the user to determine additional sounds to obtain a better match to his tinnitus. For example, after generating a sound (e.g. a first generated sound) based on the determined center frequency and the determined bandwidth as described above, the subject can elect and/or be required to generate one or more additional sounds in a similar manner (i.e. specify loudness, one or more cutoff frequencies, etc.) that can be combined with the first generated sound in any suitable manner to generate the second sound. In some embodiments, the combination is achieved by the adjustment of the relative level of the two sounds as well as the sum of the two sounds. In some embodiments, at least one additional sound can be generated. In some embodiments, at least two, at least three, at least four, at least five, and at least six additional sounds can be generated in this manner. In some embodiments, the second sound can be based on an octave-verified version of the combined sound, as described earlier. The second sound can then be applied to the subject, thereby suppressing the tinnitus of the subject.

It is understood that while embodiments disclosed herein are directed to generation of a tinnitus-suppressing sound by one of a plurality of disclosures, multiplicity of these aspects are within the scope of these embodiments. In other words, multiple candidate tinnitus-suppressing sounds can be generated, by one or more procedures, and a selection can be made there from by any suitable method disclosed herein (e.g. octave verification, likeness scoring, forced choice judgment, and/or the like). In some embodiments, at least one procedure of the plurality of procedure can be based on tinnitus suppression methods as disclosed in commonly owned U.S. Pat. No. 8,357,102 issued Jan. 22, 2013, entitled "DEVICES AND METHODS FOR SUPPRESSION OF TINNITUS", the disclosure of which is incorporated in its entirety herein by reference.

FIG. 1 illustrates an environment or system 100 within which aspects of the method can be implemented. The system 100 is configurable for at least matching the tinnitus of a subject, and can be further configurable for suppressing the tinnitus of the subject.

The system 100 includes an audio interface 102, a computing apparatus 104, an input interface 106, and a display device 108. The various components of the system 100 can be in communication as indicated by lines in FIG. 1 via wiring, via wireless means, and/or a network, which may be any type of network (e.g., a local area network or LAN, a wide area network or WAN, a virtual network, a telecommunications network, and/or the internet) implemented as a wired network and/or a wireless network. Any or all communications may be secured (e.g., encrypted) or unsecured, as is known in the art.

The audio interface 102 can be configured to deliver sound to the subject in any suitable manner. The audio interface 102 can include, but is not limited to, headphones, speakers, auditory implants, and/or the like. The audio interface 102 can further be configured to include audio controls such as, but not limited to, volume control, mute/unmute options, frequency control, and/or the like.

The input interface 106 can be configured to receive user input for at least the purposes described herein. For example, the input interface 106 can be configured to receive an indication of likeness scores as described earlier. The input interface 106 can include, but is not limited to, one or more of a keyboard, a mouse, a joystick, a touchscreen display, a rotary dial, a voice recognition component, and/or the like.

The display device 108 can be configured to display to the subject any input, output, processing, status, and/or other information associated with the various procedure(s) described herein. For example, the display device 108 can be configured to display the interface of FIG. 7 to the subject for specifying center frequency and bandwidth information. The display device 108 can include, but is not limited to, one or more of a monitor, touchscreen, a smartphone screen, a television, and/or the like.

Figure 2:
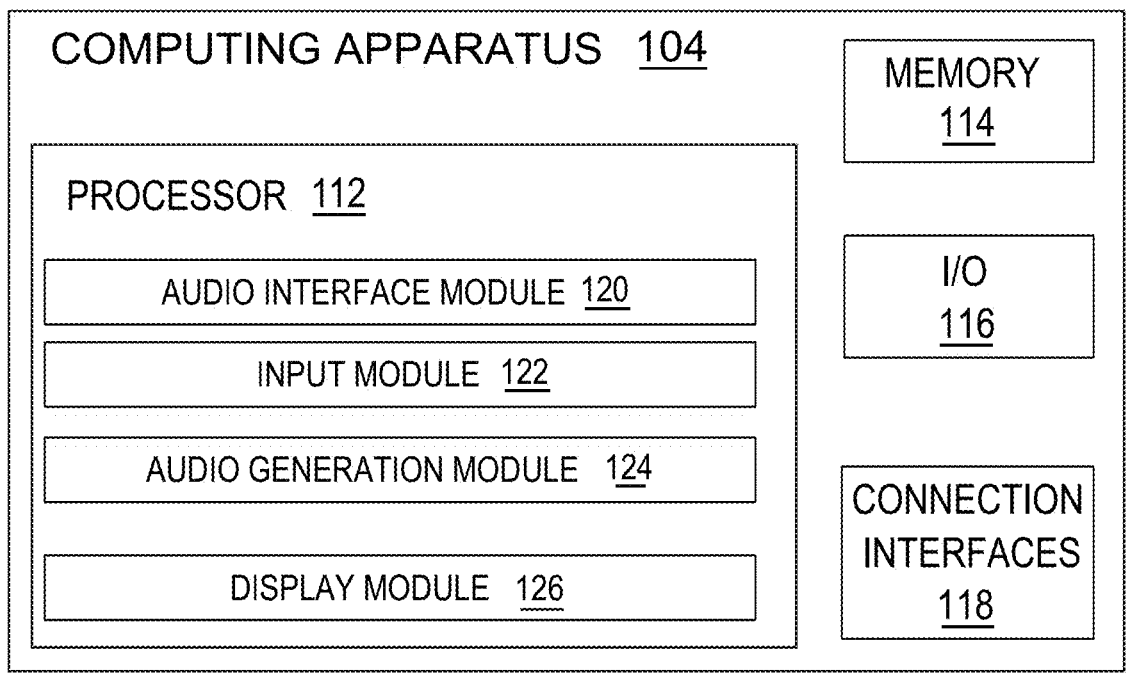
FIG. 2 is an illustration of the computing apparatus of the system of FIG. 1, according to an embodiment.

The computing apparatus 104 can be configured for matching the tinnitus of the subject, and can include one or more of a personal computer, a server, a work station, a tablet, a mobile device, a cloud computing environment, an application or a module running on any of these platforms, and/or the like. FIG. 2 illustrates the apparatus 104 of the system 100 according to some embodiments. The apparatus 104 can include at least a processor 112 and a memory 114. The apparatus 104 can also include an I/O component 116 for transmission of data and/or control signals between the various components of the apparatus 104 (e.g. a system bus), and can further include connection interfaces 118 for interface the various components of the system 100.

The processor 112 includes an audio interface module 120, an input module 122, an audio generation module 124, and a display module 126. It is understood that communication between any of the modules described herein can be restricted or unrestricted. It is further understood that any of the modules can be combined as desired/necessary without departing from the embodiments disclosed herein. Although illustrated here as implemented as part of the processor 112, in some embodiments, at least one of the audio interface module 120, the input module 122, the audio generation module 124, and the display module 126 can be implemented in one or more of a memory and a processing device The audio interface module 120 can be configured to apply a plurality of sounds to a subject, such as via the audio interface 102. The plurality of sounds can include a plurality of first sounds and further include a plurality of second sounds.

In some embodiments, the plurality of the first sounds comprises a single frequency component and the plurality of the second sounds comprises multiple frequency components. In some embodiments, the plurality of the first sounds consists of a single frequency component and the plurality of the second sounds consists of multiple frequency components. In some embodiments, the plurality of the first sounds comprises a pure tone and the plurality of the second sounds comprises multiple frequency components. In some embodiments, the plurality of the first sounds consists of a pure tone and the plurality of the second sounds consists of multiple frequency components. In some embodiments, the plurality of the first sounds comprises multiple frequency components and the plurality of the second sounds comprises multiple frequency components. In some embodiments, the plurality of the first sounds consists of multiple frequency components and the plurality of the second sounds consists of multiple frequency components. In some embodiments, the plurality of the first sounds comprises a harmonic and the plurality of the second sounds comprises multiple frequency components. In some embodiments, the plurality of the first sounds consists of a harmonic and the plurality of the second sounds consists of multiple frequency components. In some embodiments, the plurality of the first sounds comprise a pure tone having a characteristic frequency associated therewith, and the plurality of the second sounds comprises a noise having a center frequency and a bandwidth associated therewith. In some embodiments, the plurality of second sounds includes at least one white noise.

The input module 122 can be configured to receive a plurality of first likeness scores associated with the plurality of the sounds, such as via the input interface 106. Each first likeness score can be representative of the similarity of the sound associated therewith to the tinnitus of the subject.

In some embodiments, the audio generation module 124 can be configured to generate the plurality of sounds based on matched tinnitus frequency information from one or more reference subjects. The audio generation module 124 can be configured to generate at least one third sound based on at least one of the plurality of first sounds and based on at least one of the plurality of second sounds. The generating can be based on the first likeness scores associated with the plurality of sounds. In some embodiments, a sound generator (not shown) associated with the audio generation module 124, implemented in hardware and/or software, can be configured for said generating. In some embodiments, the audio generation module 124 can further include an analysis module (not shown) configured to, responsive to an input signal from the subject, determine a fourth sound based on the at least one third sound, where the fourth sound matches the tinnitus of the subject.

In some embodiments, the audio generation module 124 can be further configured to determine the loudness of the tinnitus by determining matched loudness for the plurality of the first sounds presented to the subject. The first sounds have a characteristic frequency, and each sound of the applied plurality of sounds has a loudness corresponding to the matched loudness of the first sound at a frequency closest to the first sound of the applied plurality of sounds.

In some embodiments, the audio generation module 124 can be further configured to determine the subject's hearing threshold and loudness level prior to the step of determining the loudness of the tinnitus. In some embodiments, the audio generation module 124 can be further configured to generate at least one third sound by determining the first sound having the highest likeness score of the plurality of first sounds and by determining the second sound having the highest likeness score of the plurality of second sounds. The audio generation module 124 can be further configured to generate a mixed sound based on the first sound and based on the second sound and to generate a plurality of the third sounds based on the mixed sound, each third sound having a distinct signal-to-noise ratio.

In some embodiments, the audio generation module 124 can be further configured to determine the fourth sound by receiving a second likeness score associated with each of the third sounds, where each second likeness score corresponds to the similarity of the third sound associated therewith to the tinnitus of the subject, and where the fourth sound is based on the third sound having the highest likeness score associated therewith.

In some embodiments, the audio generation module 124 can be further configured to determine the fourth sound by generating a plurality of fifth sounds based on the third sound having the highest likeness score. In some embodiments, at least one of the fifth sounds has the same frequency as the third sound having the highest likeness score, and each other fifth sound has a distinct octave of the frequency of the third sound having the highest likeness score. The audio generation module 124 can be further configured to receive a third likeness score associated with each of the third sounds, each third likeness score representative of the similarity of the third sound associated therewith to the tinnitus of the subject. In some embodiments, the fourth sound can be based on the fifth sound having the highest third likeness score associated therewith.

In some embodiments, the audio generation module 124 can be further configured to determine the fourth sound by generating a sound vector based on the fifth sound, the sound vector representative of sound characteristics of the fifth sound. The audio generation module 124 can be further configured to search a parameter space of a plurality of candidate sounds based on the sound vector and select a first candidate sound of the plurality of candidate sounds as being the closest representation of the tinnitus of the subject. The fourth sound can be generated based on the first candidate sound.

In some embodiments, the sound vector is an N-dimensional vector and the parameter space is an N-dimensional parameter space. The audio generation module 124 can be further configured to search the parameter space by searching the N-dimensional parameter space via an adaptive approach, where the adaptive approach selects the first candidate sound based on the sound vector. In some embodiments, the adaptive approach comprises an artificial neural network. In some embodiments, the sound characteristics of the fifth sound comprise one or more of the following: a center frequency, a bandwidth, a pure tone-to-noise ratio, a loudness, and a threshold.

In some embodiments, the audio generation module 124 can be further configured to determine the fourth sound by receiving a second likeness score associated with each of the third sounds. Each second likeness score can correspond to the similarity of the third sound associated therewith to the tinnitus of the subject. The fourth sound can correspond to the third sound having the highest second likeness score associated therewith.

In some embodiments, the audio interface module 120 can be further configured to apply the fourth sound to the subject, thereby suppressing the tinnitus of the subject.

In some embodiments, the audio interface module 120 can be configured to apply a sound to a subject, and the input module 122 can be configured to receive, in response to the applying: a signal indicative of a perceived loudness, and a signal identifying one or more perceived cut-off frequencies. The perceived loudness can correspond to the loudness of the tinnitus of the subject. The perceived cut-off frequencies can correspond to an upper cut-off frequency of the tinnitus of the subject, or of a lower cut-off frequency of the tinnitus of the subject, or both. In some embodiments, the audio generation module 124 can be further configured to generate the applied sound based on matched tinnitus frequency information from one or more reference subjects.

In some embodiments, the memory 114 can be constructed to store data corresponding to a characteristic frequency and a bandwidth based on the perceived cut-off frequencies. In some embodiments, the sound generator of the audio generation module 124 can generate a second sound corresponding to the tinnitus of the subject based on the perceived loudness, the characteristic frequency and the frequency bandwidth.

In some embodiments, the second sound comprises a single frequency component. In some embodiments, the second sound comprises multiple frequency components. In some embodiments, the second sound comprises a pure tone. In some embodiments, the second sound consists of a pure tone. In some embodiments, the second sound comprises a harmonic. In some embodiments, the second sound consists of a harmonic. In some embodiments, the applied sound comprises a pure tone. In some embodiments, the applied sound consists of a pure tone. In some embodiments, the applied sound comprises a single frequency component. In some embodiments, the applied sound comprises multiple frequency components. In some embodiments, the applied sound comprises a harmonic. In some embodiments, the applied sound consists of a harmonic.

In some embodiments, the specification of the perceived cut-off frequencies includes the upper cut-off frequency and the lower cut-off frequency, and the center frequency is based on the average of the upper cut-off frequency and the lower cut-off frequency. In some embodiments, the specification of the perceived cut-off frequencies includes the upper cut-off frequency and the lower cut-off frequency, and the frequency bandwidth is based on the difference between the upper cut-off frequency and the lower cut-off frequency.

In some embodiments, the input module 122 can be further configured to receive a first likeness score associated with the second sound, where the likeness score corresponds to the similarity of the second sound to the tinnitus of the subject. The audio generation module 124 can be further configured to select the second sound for applying to the subject if the first likeness score matches or exceeds a threshold, and reject the second sound if the likeness score does not match or exceed the threshold.

In some embodiments, the audio generation module 134 can be further configured to generate the second sound by generating a plurality of third sounds based on the perceived loudness, the center frequency and the frequency bandwidth. At least one of the third sounds has the center frequency, and each other third sound has a distinct octave of the center frequency. A second likeness score associated with each of the third sounds can be received, where each third likeness score corresponds to the similarity of the third sound associated therewith to the tinnitus of the subject. The second sound can be based on the third sound having the highest second likeness score associated therewith.

In some embodiments, the audio generation module 134 can be further configured to generate the second sound by generating a first sound component that matches a first perceived component of the tinnitus of the subject based on the perceived loudness, the center frequency and the frequency bandwidth, and to generating one or more additional sound components, where each additional sound component corresponds to an additional perceived component of the tinnitus of the subject. A mixed sound can be generated based on the first sound component and based on the additional sound components, and the second sound can be generated based on the mixed sound. In some embodiments, each sound component can comprise a different characteristic from each other sound component and different from the third sound in one or more of the following aspects: a loudness of the sound component, a center frequency of the sound component, and a frequency bandwidth of the sound component.

In some embodiments, the audio generation module 134 can be further configured to generate the second sound by generating a plurality of third sounds based on the mixed sound, where at least one of the third sounds has the center frequency of the mixed sound, and where each other third sound has a distinct octave of the center frequency of the mixed sound. A likeness score associated with each of the third sounds can be received, where each likeness score corresponds to a similarity of the third sound associated therewith to the tinnitus of the subject. The second sound can correspond to the third sound having the highest likeness score associated therewith.

The audio interface module 120 can be further configured to apply the third sound to the subject, thereby suppressing the tinnitus of the subject.

Figure 3:
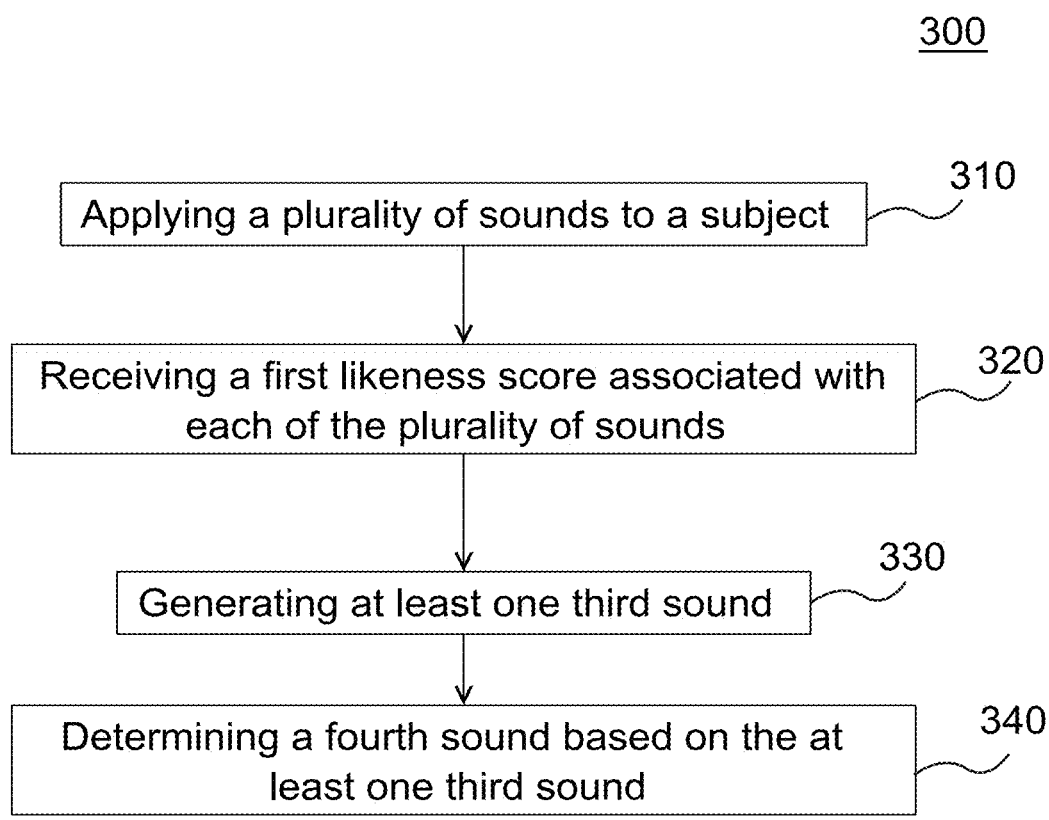
FIG. 3 is a method of the invention of matching the tinnitus of a subject, according to an embodiment.

FIG. 3 illustrates a method 300 for matching of tinnitus of a subject, according to some embodiments. In some embodiments, aspects of the method 300 can be realized by the computing apparatus 104. In some embodiments, computer readable storage media stores computer executable instructions for implementing the method 300. At 310, a plurality of sounds are applied to a subject. The plurality of sounds can comprise a plurality of first sounds and further comprise a plurality of second sounds. At 320, a first likeness score associated with the plurality of the sounds are received. Each first likeness score can be representative of the similarity of the sound associated therewith to the tinnitus of the subject. At 330, at least one third sound based on at least one of the plurality of first sounds and based on at least one of the plurality of second sounds is generated based on the first likeness scores associated with the plurality of sounds. At 340, a fourth sound based on the at least one third sound is determined, wherein the fourth sound matches the tinnitus of the subject.

Figure 4:
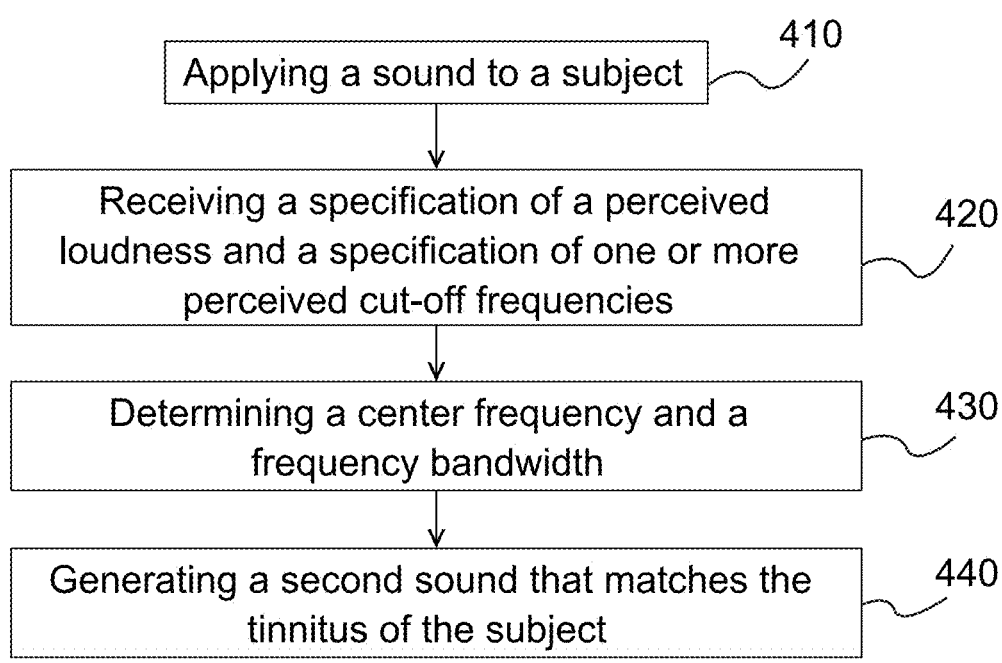
FIG. 4 is another method of the invention of matching the tinnitus of a subject, according to an embodiment

FIG. 4 illustrates a method 400 for matching of tinnitus of a subject, according to some embodiments. In some embodiments, aspects of the method 400 can be realized by the computing apparatus 104. In some embodiments, computer readable storage media stores computer executable instructions for implementing the method 400. At 410, a sound can be applied to a subject. At 420, a specification of a perceived loudness and a specification of one or more perceived cut-off frequencies can be received. The perceived loudness can correspond to the loudness of the tinnitus of the subject. the perceived cut-off frequencies can correspond to an upper cut-off frequency of the tinnitus of the subject, or to a lower cut-off frequency of the tinnitus of the subject, or both. At 430, a center frequency and a frequency bandwidth based on the perceived cut-off frequencies can be determined. At 440, a second sound that matches the tinnitus of the subject based on the perceived loudness, the center frequency and the frequency bandwidth can be generated.

In some embodiments described herein, a computer storage product with a non-transitory computer-readable medium (also referred to as a non-transitory processor-readable medium) has instructions or computer code thereon for performing various computer-implemented operations. The computer-readable medium (or processor-readable medium) is non-transitory in the sense that it does not include transitory propagating signals (e.g., a propagating electromagnetic wave carrying information on a transmission medium such as space or a cable). The media and computer code (also referred to herein as code) may be those designed and constructed for the specific purpose or purposes. Examples of non-transitory computer-readable media include, but are not limited to: magnetic storage media such as hard disks, optical storage media such as Compact Disc/Digital Video Discs (CD/DVDs), Compact Disc-Read Only Memories (CD-ROMs), magneto-optical storage media such as optical disks, carrier wave signal processing modules, and hardware devices that are specially configured to store and execute program code, such as Application-Specific Integrated Circuits (ASICs), Programmable Logic Devices (PLDs), Read-Only Memory (ROM) and Random-Access Memory (RAM) devices.

Examples of computer code include, but are not limited to, micro-code or micro-instructions, machine instructions, such as produced by a compiler, code used to produce a web service, and files containing higher-level instructions that are executed by a computer using an interpreter. For example, embodiments may be implemented using Java, C++, or other programming languages and/or other development tools.

The various embodiments described herein should not to be construed as limiting this disclosure in scope or spirit. It is to be understood that no limitation to the scope of the disclosure is intended thereby. It is to be further understood that resort may be had to various other embodiments, modifications, and equivalents thereof which may suggest themselves to those skilled in the art without departing from the spirit of the present disclosure and/or scope of the appended claims.

Those skilled in the art will recognize, or be able to ascertain, using no more than routine experimentation, numerous equivalents to the specific embodiments described specifically herein. Such equivalents are intended to be encompassed in the scope of the following examples and claims.

EXAMPLES

Experiment 1

Normal Hearing Subjects with Tinnitus Simulation

Due to the subjective nature of tinnitus, it is difficult to evaluate the accuracy and efficiency of a tinnitus matching procedure. Here we present a well-defined objective sound to the subject as the standard tinnitus and ask subjects to match the sound using the tinnitus matching methods developed here. We thus create a gold standard to evaluate the accuracy of outcomes from these matching methods. The aim of Experiment 1 is to evaluate adaptive and adjustment Tinnitus Matching Procedures by comparing the matched outcomes to a known, simulated tinnitus in normal hearing subjects.

Materials and Methods
Subjects.

53 normal hearing subjects (26M, 27 F) were recruited from the undergraduate student population at the University of California, Irvine; ages ranged from 18 to 26 years of age.

Stimuli.

Figure 5A:
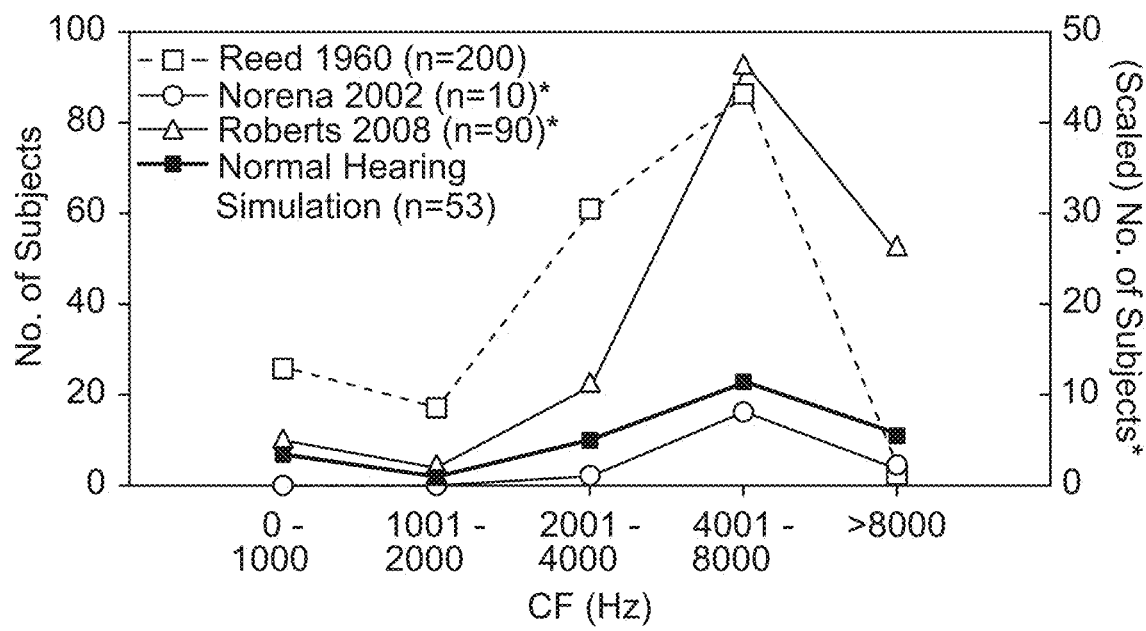
FIGS. 5A-5B are histograms of (FIG. 5A) Tinnitus Center Frequencies (CF) and (FIG. 5B) Tinnitus Bandwidths from actual tinnitus patients. Distributions of CFs and bandwidths of tinnitus patients are shown for studies by Reed 1960 (open squares), Norena 2002 (open circles) and Roberts 2008 (open triangles). Simulated tinnitus stimuli designed for this study are shown (filled squares, with thick black line). Bandwidth was not measured for Norena 2002, which only tested patients with tonal tinnitus. The number of subjects corresponding to each category is shown on the left-sided Y-axis; the asterisk in the legend indicates studies corresponding to the scaled number of subjects on the right-sided Y-axis.
Figure 5B:
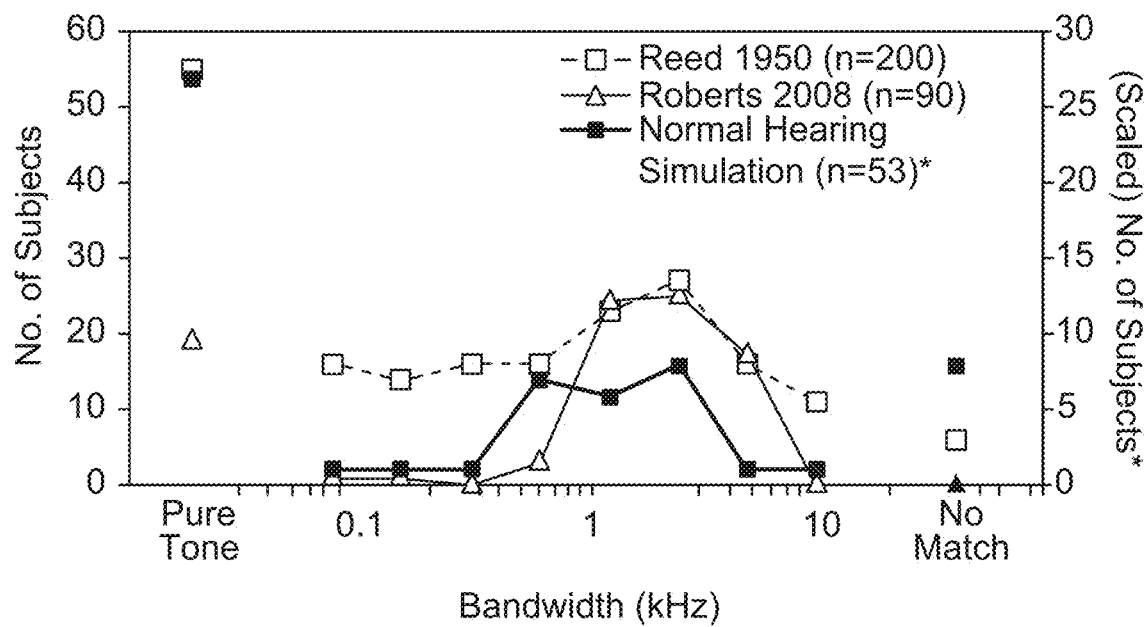

Simulated tinnitus sounds were designed using tinnitus matches from actual patients as a reference (Reed, 1960; Norena et al., 2002; Roberts et al., 2008). Distributions of the tinnitus matched results are shown in FIGS. 5A-5B, with the majority of patients matching tinnitus to center frequencies (CFs) within 4000-8000 Hz (FIG. 5A) and bandwidths within 2400-4800 Hz range (FIG. 5B). Accordingly, one-third of our stimuli were designed as pure tones (36%; 19 of 53 sounds), and nearly half of our stimuli fell into the 4000-8000 Hz frequency range (43%; 23 of 53 sounds).

Simulated tinnitus stimuli were played continuously for the duration of the tinnitus matching procedure. Each stimulus contained a ramped sound (pure tone or noise) of 0.5 seconds duration, followed by a 1 second gap of silence. Simulated tinnitus was presented to the left ear, while sounds used for tinnitus matching were delivered to the right ear. All sounds were presented using Sennheiser HDA-200 headphones (Wedemark, Germany).

Procedures.

Subjects were single-blinded and assigned a simulated tinnitus sound as a standard, and asked to match their assigned sound using the adjustment and adaptive tinnitus matching methods developed here. An octave verification step was added for both procedures for the latter 28 subjects tested, and 14 subjects were asked to repeat both procedures a total of 3 times each to attain reliability measures of the matched sound.

Tinnitus Matching Procedures.

Two computer-based procedures have been developed in this study to optimize tinnitus matching. The first is a thorough and controlled adaptive procedure which walks the subject step-wise through several discrete aspects of tinnitus matching. The second is an adjustment procedure, which allows the subject flexible control to match several aspects of their tinnitus. Tinnitus matching software here were written and run using the MATLAB platform, version 7.1.0.246 (R14) Service Pack 3 (MathWorks; Natick, Mass., U.S.A.) on a Dell Latitude E6510 laptop and delivered using Sennheiser HDA-200 headphones (Wedemark, Germany). The system was calibrated acoustically using a B&K Type 2260 sound level meter in a Zwislocki real-ear stimulator (Narum, Denmark).

1) Adaptive Procedure

Figure 24:
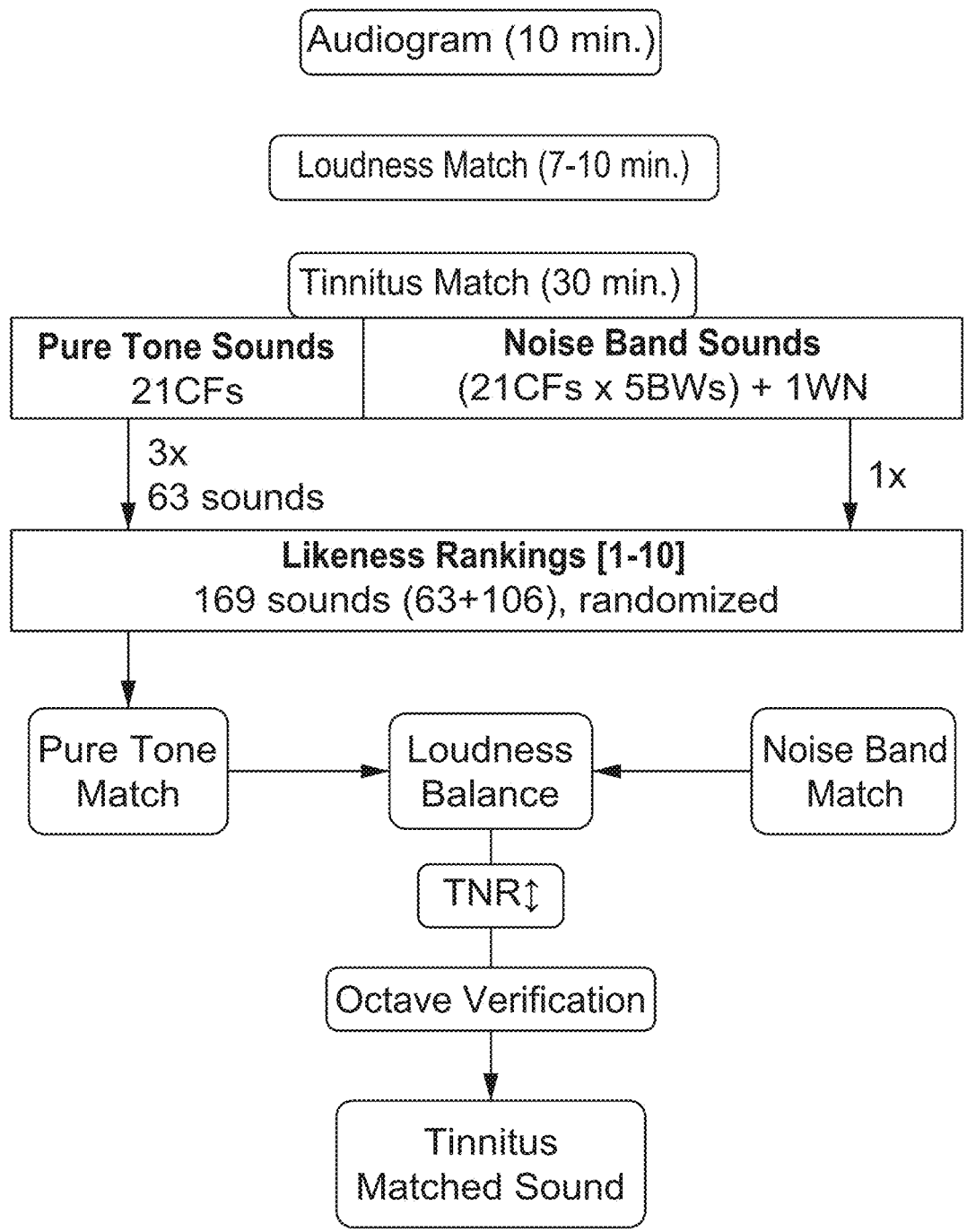
FIG. 24 is a schematic for optimized tinnitus matching for an adaptive procedure.

The "adaptive" procedure leads the tinnitus subject through the following discrete steps to find a tinnitus match (see FIG. 24):

1. Audiogram. A "method of limits" procedure is used to find thresholds of 11 pure tones from 500 Hz to 16 kHz in half-octave steps. Each sound begins from a sub-threshold level and increases stepwise by 5 dB until the subject responds to indicate that the sound is perceptible. The sound then increases by 10 dB and decreases stepwise by 5 dB until the subject responds to indicate that the sound is imperceptible. The two response levels are then averaged to find the subject's threshold.

2. Equal Loudness Matching. Next, the subject is asked to adjust the sound level of 11 pure tones from 500-16 k in half-octave steps. Subjects are asked to adjust the volume of each sound to be: just noticeably louder than their tinnitus, just noticeably softer than their tinnitus, and equal loudness to their tinnitus.

Figures 6, 7:
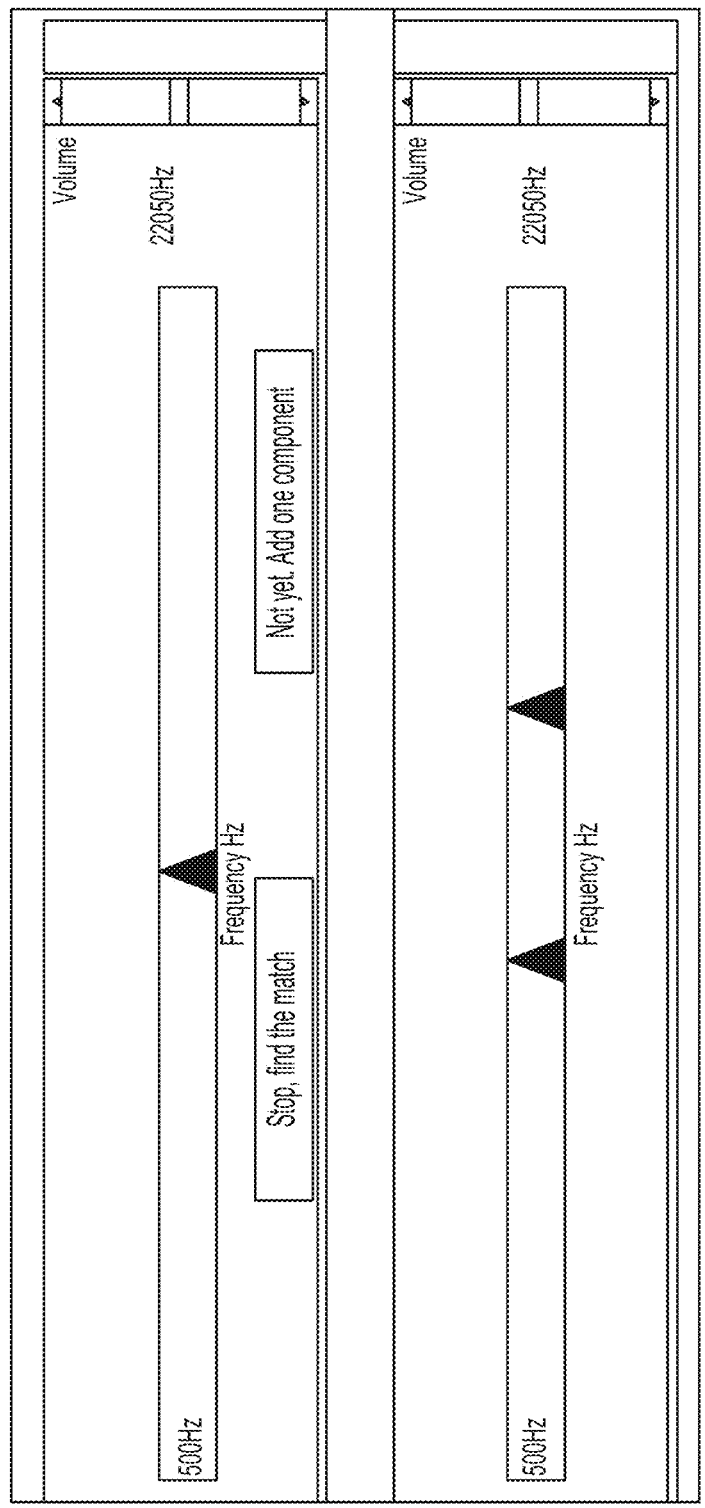
FIG. 6 is an illustration of a response bar for tinnitus likeness ratings in the adaptive method interface. Subjects were presented with a shaded bar with the question "How similar is the sound to your tinnitus?" Subjects were instructed to click on the region of the shaded bar corresponding to their response.
FIG. 7 is an illustration of an adjustment method user-controlled interface. The interface for the adjustment method of tinnitus matching is shown here. The shaded bar represents frequencies from 500 Hz (left) to 22050 Hz (right). The triangles on the shaded bar represent the lower and upper cutoff frequencies (left and right triangles, respectively). Thus, the distance between the triangles represents the bandwidth of the presented sound, or a pure tone if the triangles are overlapping (as in the upper panel). Volume controls are shown to the right of each frequency bar for each sound component. Two components are shown here to the matched sound (upper and lower panels); subjects are able to add up to 3 sound components using this interface.

3. Tinnitus Likeness. Subjects are asked to rank the similarity of loudness-matched sounds to their tinnitus, using equal loudness-responses from the previous step. Sounds at twenty-one CFs from 500 Hz to 16 kHz in quarter-octave steps; and at six bandwidths of $\{0, 0.0625, 0.125, 0.25, 0.5$ and $1\}$-octave bandwidths will be presented in a random order, including a white-noise stimulus (see Appendix A). Pure tones will be presented three times each. For each sound, the subject is asked to first verify that the sound is equal in loudness to their tinnitus. (If not, the subject is encouraged to make adjustments accordingly). Then, the subject is asked to rank the similarity of the presented sound to their tinnitus by clicking their response on the corresponding region of the response bar (FIG. 6).

4. Verifying Threshold and Loudness Matching. The highest ranked pure tone and the highest ranked noise from the previous step are selected as the final two sounds for tinnitus matching. In this step, thresholds and equal-loudness matching for these two sounds are repeated.

5. Tone-in Noise Ratio. The best pure tone and the best noise will be mixed at different signal-to-noise ratios and presented to the subject for similarity ratings (identical procedure as Step 3). Presented signal-to-noise ratios include: $\{0, \pm 5, \pm 10, \pm 15, \pm 20, \pm 25, \pm 30, \pm 35, \pm 40, \pm \text{Inf}\}$.

6. Octave Verification. The highest ranked sound from Step 5 is presented at the original octave, 1-octave lower, and 1-octave higher for octave verification. The sounds are played in pairs in a random order, for a 2-AFC judgment by the subject to determine the closest octave of the matched sound to their tinnitus.

2) Adjustment Procedure

The "adjustment" procedure provides a flexible interface for the tinnitus subject to find the best match of their tinnitus (see FIG. 6). The interface for this procedure is completely user controlled, and allows the user to flexibly adjust: (1) frequency, (2) bandwidth, and (3) volume. The user is presented with a shaded frequency bar, representing frequencies from low (500 Hz) to high (22050 Hz). The frequency bar contains two triangles—the left triangle represents the lower-cutoff frequency, while the right triangle represents the upper-cutoff frequency. By shifting the relative position of the triangles on the shaded frequency bar, the subject can adjust the frequency of the matched sound. Second, the distance between the triangles can be adjusted to change the bandwidth of the sound. The further apart the triangles are, the wider the bandwidth of sound; if the triangles are overlapping, the sound represented is a puretone. Third, the user can adjust the volume of the matched sound by adjusting the volume control. Adjustment of these three parameters can allow the subject to find a best sound to match their tinnitus. Lastly, a built-in feature of this program allows the subject to add additional sound components (up to 3) if additional sound components are present in their tinnitus.

Subjects are given the option to "Add one component;" if selected, a dialog identical to the initial one presented will appear, allowing the subject to add up to 3 sound components to best match their tinnitus.

Once the subject finds the best match, they are asked to rank the similarity of this matched sound to their tinnitus. (The rating bar is identical to the one used in the "adaptive" match; see FIG. 7). Lastly, this matched sound is presented at the original octave, at one-octave lower and one octave higher. Subjects are asked to loudness match each of these sounds to their tinnitus, and then select the sound that is closest to their tinnitus.

All normal hearing subjects gave informed, written consent and received course credit for their participation. Protocols were approved by the Institutional Review Board at the University of California Irvine.

Analysis.

Statistical methods were used to compare outcomes of the tinnitus matching methods. Prior to statistical analyses, appropriate adjustments and transformations were applied to compensate for the logarithmic spacing of acoustic frequencies: averages of acoustic frequencies were calculated as geometric means, and frequencies of the pitch matched results were log transformed prior to statistical analyses. Where relevant, dB SPL measurements were converted to dB HL units using the ANSI S3.6-2004 Conversion Table for Sennheiser HAD200 Headphones (American National Standards Institute, 2004). Pearson Correlation analyses were used to compare CFs of the tinnitus match to that of the actual sound and from different matching methods Tinnitus rating outcomes of the various tinnitus matching methods were evaluated using the nonparametric Friedman Test for analyses of variance by ranks ($\chi2$), followed by post-hoc analyses with Wilcoxon Signed-Rank Test with Bonferroni correction. Repeated measures ANOVAs with Greenhouse-Geisser corrections were used to compare log transformed frequencies to compare pitch matching results and time costs from different tinnitus matching methods. Significance levels were set at 0.05. All statistical analyses were conducted using the SPSS software (PASW Statistics 18; Somers, N.Y.).

Results

Figure 8A:
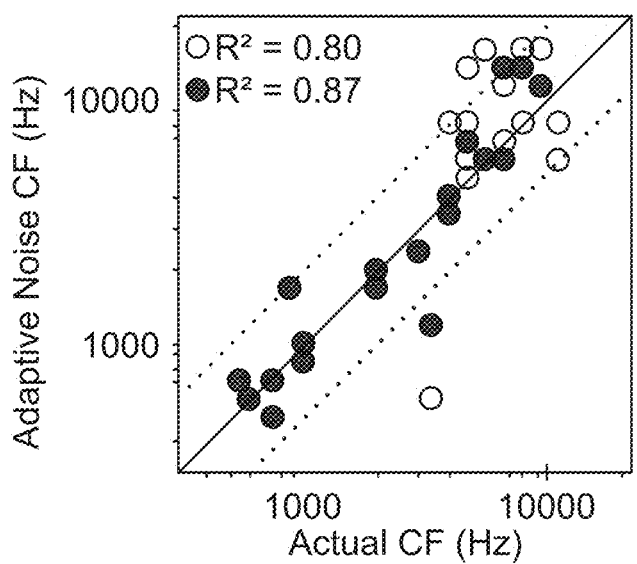
FIGS. 8A-8C are plots of the correlation of Center Frequencies (CFs) between the actual tinnitus simulation sound versus outcomes from the Adaptive (FIGS. 8A, 8B) and Adjustment (FIG. 8C) tinnitus matching procedures. The matched CFs of the best matched noise (FIG. 8A) and tone (FIG. 8B) from the Adaptive Procedures, and of the matched sound from the Adjustment Procedure (FIG. 8C) is shown plotted against the actual CF of the simulated tinnitus sound (x-axis). The original matched CF (prior to octave verification) is shown in open circles, while the octave verified CF of the matched CF is shown in the upper left corner of each panel, with the $R_2$ of the octave verified tinnitus match beneath it. The solid line represents the equivalence line between the actual and matched CFs; dotted lines represent CFs corresponding to one-octave above and below the actual CF.
Figure 8B:
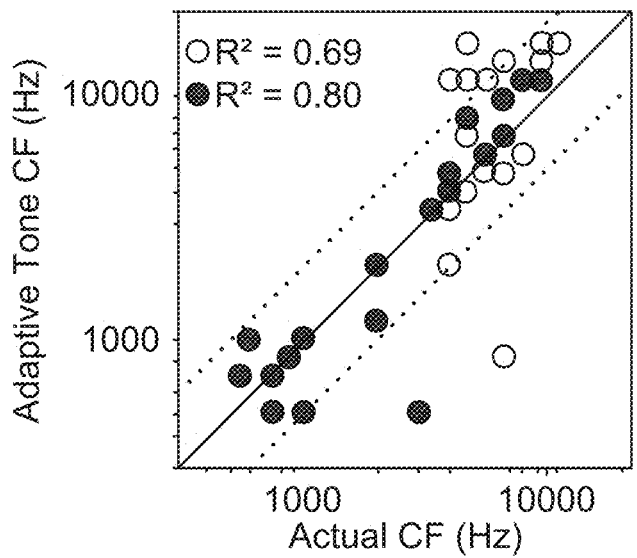
Figure 8C:
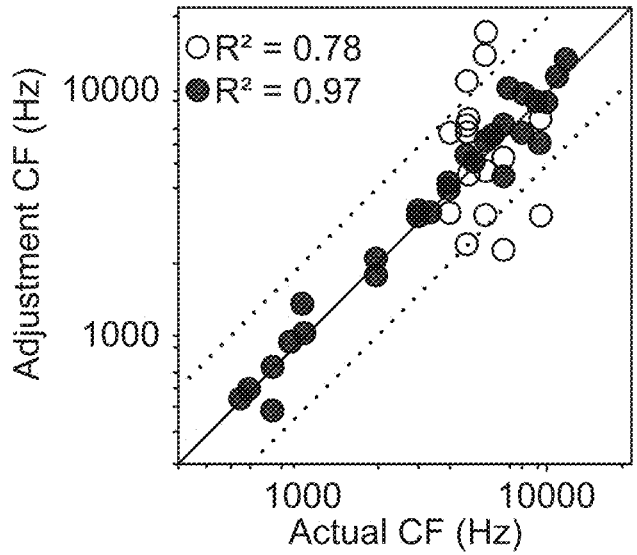

FIGS. 8A-8C compares the center frequency of the matched sound to the center frequency of the actual presented sound, showing the original match (open circles) and the match following octave verification (filled circles). In FIG. 8A, the center frequency of the best matched noise from the Adaptive Procedure is shown plotted against the actual center frequency of the simulated tinnitus. The correlation of the original tinnitus match is $R_2=0.80$, $p<0.001$, which increases to $R_2=0.87$, $p<0.001$ following octave verification. In FIG. 8B, the center frequency of the best matched tone from the Adaptive Procedure is shown plotted against the actual center frequency of the simulated tinnitus. The correlation of the tinnitus match of the best matched tone is the lowest of the three outcomes, at $R_2=0.69$, $p<0.001$, increasing to $R_2=0.80$, $p<0.001$ following octave verification. Lastly, the center frequency of the self-matched Adjustment Procedure is shown plotted against the actual center frequency of the simulated tinnitus in FIG. 8C. The correlation of the tinnitus match of the best matched tone is originally at $R_2=0.78$, $p<0.001$, which increases to the highest matching accuracy at $R_2=0.97$, $p<0.001$ following octave verification. Thus the octave verification step provides a clear benefit in improving the accuracy of the outcome of the tinnitus match.

Figure 9A:
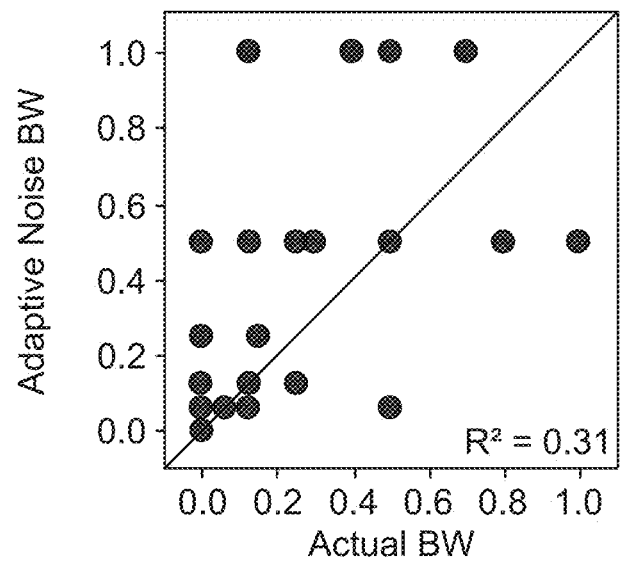
FIGS. 9A-9B are plots of the correlation of Matched Bandwidths (BW) between the actual tinnitus simulation sound versus outcomes from the Adaptive Match (FIG. 9A) and Adjustment Match (FIG. 9B). The matched BWs of the best matched noise from the Adaptive (FIG. 9A) and Adjustment (FIG. 9B) Procedures are shown plotted against the actual BW. The Pearson correlation coefficient ($R_2$) of the matched bandwidth to the actual bandwidth of the simulated tinnitus is shown in the bottom right corner. The solid line indicates equivalent bandwidth between the actual and matched tinnitus sounds.
Figure 9B:
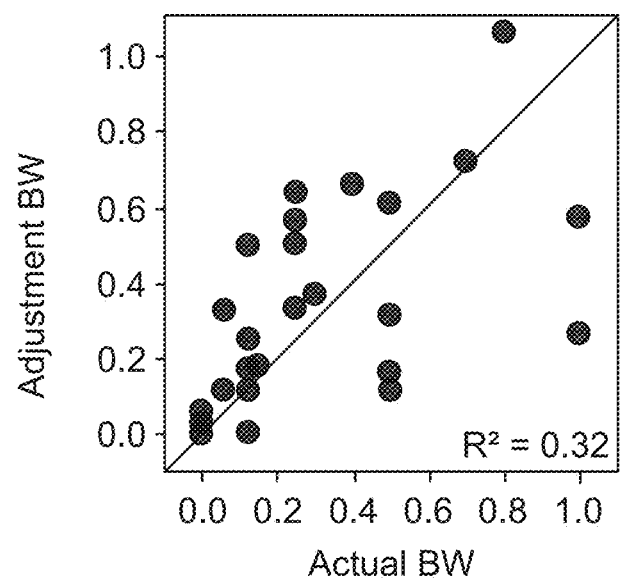

Bandwidth comparisons between the matched sound and actual bandwidths from the tinnitus simulation sound were also evaluated (FIGS. 9A-9B). The Pearson correlation coefficient ($R_2$) of the actual bandwidth to the adaptive noise yielded correlation $R_2=0.31$, $p<0.001$, while correlation to the adjustment method yielded correlation $R_2=0.32$, $p<0.001$. No particular difference was noted in the accuracy of matching bandwidth between these two methods; bandwidth appears to be a difficult acoustic index to measure for these subjects.

Figure 10:
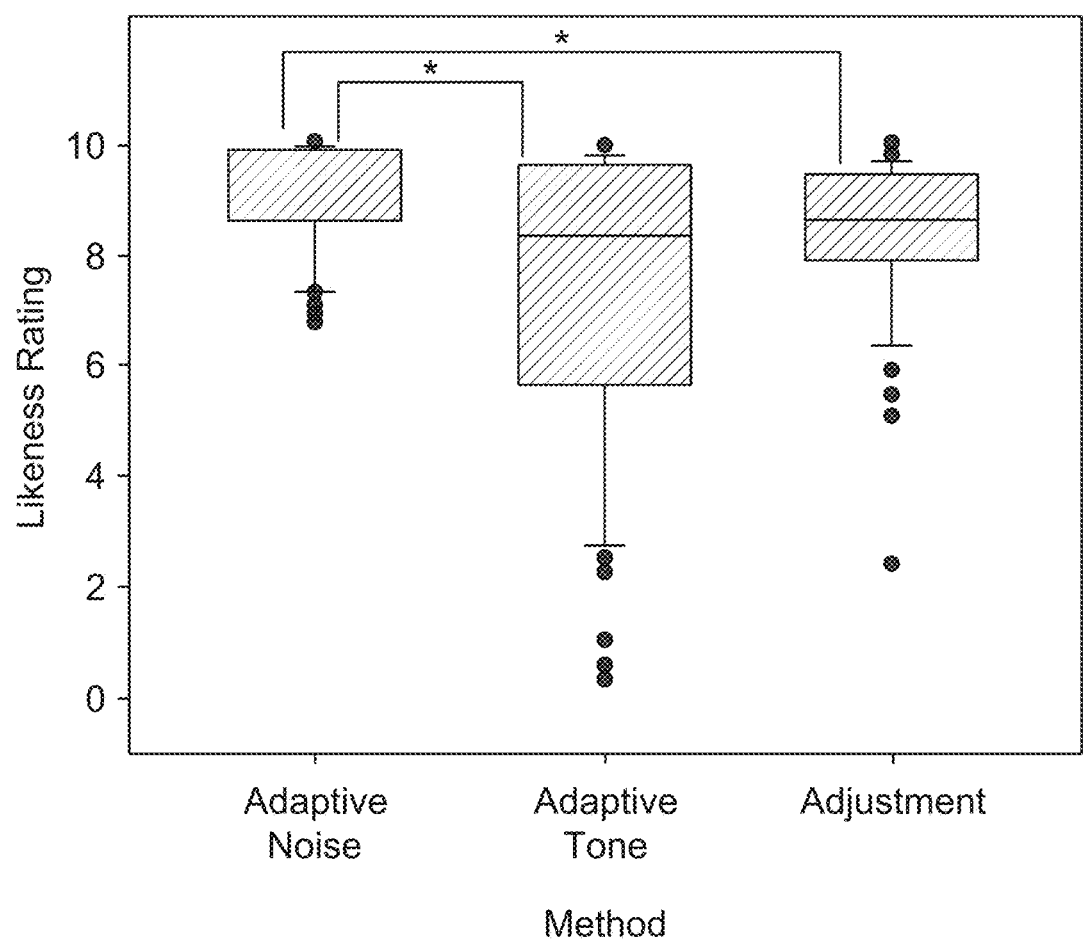
FIG. 10 is a plot of likeness ratings of matched sounds in normal hearing simulation, by method. Box plots showing the likeness rating of the best matched sound is shown by method for the best matched noise and tone from the Adaptive Procedures, and the Adjustment Procedure (left to right).

FIG. 10 compares tinnitus likeness ratings from the different methods. There was a statistically significant difference in the tinnitus likeness ratings across methods, $\chi_2(2)=7.626$, $p=0.022$ (Friedman Test for non-parametric repeated measures ANOVA). Median likeness ratings were highest for the adaptive noise match at 9.6, which was statistically higher than both ratings from the adaptive tone match of 8.7 and from the adjustment method of 8.5, per post-hoc analyses with Wilcoxon Signed-Rank Tests ($Z=-3.776$, $p=0.000$; and $Z=-2.211$, $p=0.027$, respectively). Although the adaptive noise procedure yields a significantly higher tinnitus likeness ranking here as compared to the adaptive noise and adjustment methods, note that the adjustment procedure provides a more accurate match to the actual CF ($R_2=0.97$) when compared to the adaptive noise ($R_2=0.87$) and adaptive tone ($R_2=0.80$) matches. While there may be some degree of variability in using the tinnitus likeness ratings as an indicator of tinnitus match accuracy, it is clear is that the introduction of bandwidth with the adaptive noise and adjustment methods decreases the spread of tinnitus likeness ratings (9.0-9.9 and 7.9-9.3 for $25^{th}$-$75^{th}$ percentile rankings for the adaptive noise and adjustment procedures, respectively) as compared to that of the puretone based adaptive tone method (6.1 to 9.8). This is indicative of a generally higher level of subject satisfaction to tinnitus matched outcomes with the incorporated bandwidth dimension, as compared to matching to a pure-tone match alone, which is consistent with improved accuracy of the resulting CF match with the bandwidth component.

Experiment 2

Tinnitus Subjects

As such, the matched outcomes to a standard, known "tinnitus" in Experiment 1 indicate that addition of the bandwidth dimension of tinnitus matching improves the accuracy of the resulting match. The aim of Experiment 2 is to compare tinnitus matched outcomes from the Adaptive and Adjustment Tinnitus Matching Procedures, along with an existing "Classic" procedure, in actual tinnitus subjects.

Materials and Methods

Subjects.

Subjects who had perceived their tinnitus for a minimum of 6 months, and were over 18 years of age were screened for the study. Prior to enrollment, subjects completed an online tinnitus survey, which included the Hearing Handicap Inventory (Ventry and Weinstein, 1982), Tinnitus Severity Index (Folmer et al., 2004), Tinnitus Handicap Index (Newman et al., 1996), Beck Anxiety Inventory (Beck et al., 1988), and Beck Depression Inventory (Beck et al., 1996). Subjects who had a treatable type of tinnitus, were actively taking known ototoxic medications, had active or recent outer or middle ear disease, were on medications or other treatments for their tinnitus, or were severely depressed were excluded from the study.

Twenty-one subjects with tinnitus, three females and eighteen males of average age 55.2±12.9 years (mean±SD; range: 32-76 years) were enrolled in the study (Table 2.1). With the exception of T01 and T02, who had each received a cochlear implant for sudden unilateral tinnitus and sensorineural hearing loss, no subjects used assistive listening devices in their daily lives. Average PTA/hearing loss across all subjects was 11, 16, 19, 31, 39, 27 dB HL at 500, 1 k, 2, 4, 8, and 16 k Hz respectively.

TABLE 1

Subject Demographics

| | | | Pure-Tone Audiogram (dB HL) | | | | | |
|---|---|---|---|---|---|---|---|---|
| Subject | Gender | Age | 500 Hz | 1 kHz | 3 kHz | 4 kHz | 8 kHz | 16 kHz |
| T01* | M | 52 | 7 | 12 | 8 | 11 | 18 | 29 |
| T02* | F | 42 | −1 | 7 | 8 | 1 | −5 | 19 |
| T22 | M | 50 | 7 | 15 | 26 | 58 | 58 | 34 |
| T35 | M | 71 | 7 | 12 | 18 | 72 | 72 | 34 |
| T66 | M | 38 | 7 | 12 | 13 | 3 | 30 | 34 |
| T70 | M | 46 | 7 | 12 | 13 | 23 | 3 | 32 |
| T71 | M | 76 | 9 | 15 | 18 | 26 | 23 | 29 |
| T72 | M | 44 | 7 | 12 | 13 | 3 | 8 | 24 |
| T73 | M | 59 | 17 | 17 | 18 | 58 | 74 | 34 |
| T76 | M | 76 | 22 | 15 | 51 | 70 | 74 | 32 |
| T77 | M | 52 | −1 | 27 | 21 | 28 | 55 | 29 |
| T78 | M | 69 | 14 | 20 | 48 | 72 | 74 | 34 |
| T79 | M | 61 | 12 | 22 | 23 | 21 | 33 | 34 |
| T81 | M | 58 | 9 | 15 | 21 | 33 | 40 | 34 |
| T82 | F | 63 | 14 | 15 | 11 | 18 | 50 | 17 |
| T83 | M | 35 | 7 | 15 | 16 | 6 | 23 | 24 |
| T84 | M | 64 | 14 | 12 | 11 | 18 | 50 | 12 |
| T85 | M | 51 | 14 | 17 | 16 | 31 | 62 | 34 |
| T86 | M | 67 | 17 | 17 | 16 | 66 | 53 | 34 |
| T87 | F | 53 | 39 | 42 | 31 | 36 | 30 | 34 |
| T88 | M | 32 | 7 | 12 | 13 | 8 | −8 | −14 |

*T01 and T02 had normal hearing in one ear, and a cochlear implant in the other

Tinnitus Characteristics.

Subject tinnitus characteristics are shown in Table 2.2. Subjects were asked to categorize their tinnitus prior to tinnitus matching; eight (38%) selected their tinnitus as "Non-Tonal" while thirteen (62%) selected "Tonal." Six (29%) subjects perceived unilateral tinnitus; 3 in the right ear only and 3 in the left ear only. Six (29%) subjects perceived bilateral but asymmetrical tinnitus, and the remaining nine (43%) perceived bilateral symmetrical tinnitus. Most subjects perceived only one distinct sound component of their tinnitus (n=14; 67%), while seven subjects perceived more than one—and up to 5 distinct sounds to their tinnitus. On average, subjects had experienced tinnitus for an average of 11.2±14.8 years (mean±SD; range: 1-52 years); and for a minimum of 6 months as part of the inclusion criteria.

TABLE 2

Subject Tinnitus Characteristics

| Subject | Tinn. Type | Tinn. Ear | # Tinn. Sounds | Tinn. Dur. (yr) | HHI | TSI | THI | BAI | BDI | Music |
|---|---|---|---|---|---|---|---|---|---|---|
| T01* | NT | R only | 2-3 | 8 | n.a. | 33 | 52 | 16 | 36 | Yes |
| T02* | NT | L only | 2 | 2 | 102 | 60 | 84 | 8 | 42 | No |

TABLE 2-continued

Subject Tinnitus Characteristics

| Subject | Tinn. Type | Tinn. Ear | # Tinn. Sounds | Tinn. Dur. (yr) | HHI | TSI | THI | BAI | BDI | Music |
|---------|------------|-----------|----------------|-----------------|------|------|------|------|------|-------|
| T22 | T | L = R | 1 | 17 | n.a. | 23 | 12 | 4 | 32 | No |
| T35 | NT | L > R | 1 | 25 | n.a. | 11 | 8 | 0 | 24 | No |
| T66 | T | L = R | 1 | 2 | n.a. | 43 | 82 | 7 | 27 | Yes |
| T70 | NT | R only | 2 | 21 | n.a. | 30 | 46 | 0 | 23 | No |
| T71 | NT | L only | 1 | 3 | 0 | 22 | 30 | 0 | 23 | Yes |
| T72 | T | L only | 1 | 6 | 0 | 16 | 6 | 2 | 23 | No |
| T73 | T | R > L | 1 | 2 | 10 | 24 | 38 | 0 | 24 | No |
| T76 | T | L > R | 1 | 22 | 38 | 36 | 40 | 5 | 28 | No |
| T77 | T | R only | 1 | 1 | 28 | 32 | 36 | 4 | 28 | No |
| T78 | T | L > R | 1 | 5 | n.a. | n.a. | n.a. | n.a. | n.a. | No |
| T79 | T | L > R | 1 | 6 | 0 | 28 | 8 | 0 | 22 | No |
| T81 | T | L = R | 1-2 | 1 | 8 | 30 | 26 | 2 | 23 | No |
| T82 | T | L = R | 1 | 3 | 2 | 19 | 10 | 7 | 23 | Yes |
| T83 | T | L = R | 1 | 1 | 14 | 35 | 66 | 5 | 35 | No |
| T84 | NT | L = R | 2 | 52 | 32 | 31 | 24 | 3 | 27 | No |
| T85 | T | L = R | 1-5 | 1 | 72 | 46 | 86 | 2 | 36 | No |
| T86 | NT | L = R | 1 | 47 | 24 | 28 | 23 | 0 | 22 | No |
| T87 | NT | L = R | 1-3 | 1 | 0 | 56 | 88 | 3 | 28 | No |
| T88 | T | L > R | 1 | 10 | 12 | 40 | 52 | 28 | 35 | Yes |

HHI: Hearing Handicap Inventory; TSI: Tinnitus Severity Index; THI: Tinnitus Handicap Index; BAI: Beck Anxiety Inventory; BDI: Beck Depression Inventory; n.a: not available
*T01 and T02 had normal hearing in one ear, and a cochlear implant in the other Procedures.

Each tinnitus subject was asked to match their tinnitus using the Adaptive and Adjustment procedures described above (see *Tinnitus Matching Procedures in Experiment* 1, above). A third "classic" tinnitus match based on procedures developed by Vernon and Meikle (2003), was introduced to compare outcomes to an existing tinnitus matching method. This procedure relies on a series of two-alternative forced choice (2-AFC) judgments by the subject to find the best match, as described below:

"Classic" Procedure

For the "classic" procedure, we followed the 2-AFC matching protocol as established by and detailed in Vernon and Meikle (1988). Briefly, the procedure starts at 1000 Hz and progresses in ascending 1000-Hz steps. Two loudness-matched sounds are presented in rapid succession and the subject chooses which is closer to his tinnitus. The procedure continues until the subject chooses the lower-frequency sound as closer to their tinnitus; then octave confusion will compare the final sound to the sound an octave above.

For all tinnitus matching procedures conducted here, the tinnitus matching ear was generally chosen as the ear ipsilateral to the dominant side of tinnitus. If the subject had unilateral or asymmetric tinnitus, the side with dominant tinnitus was chosen as the tinnitus matching ear. If the subject had bilaterally equal tinnitus, the side with better hearing was chosen as the tinnitus matching ear. For the two subjects with cochlear implants and unilateral deafness and tinnitus (T01 and T02), the non-implanted ear, which was contralateral to the tinnitus ear, was chosen as the tinnitus matching ear. Tinnitus matching procedures were completed by the subjects in a randomized order.

All subjects gave informed, written consent and protocols were approved by the Institutional Review Board at the University of California Irvine.

Analysis.

Analysis techniques were comparable to those used in Experiment 1. Please see "Analysis" under Experiment 1 for details on analysis methods.

Results

Figure 11:
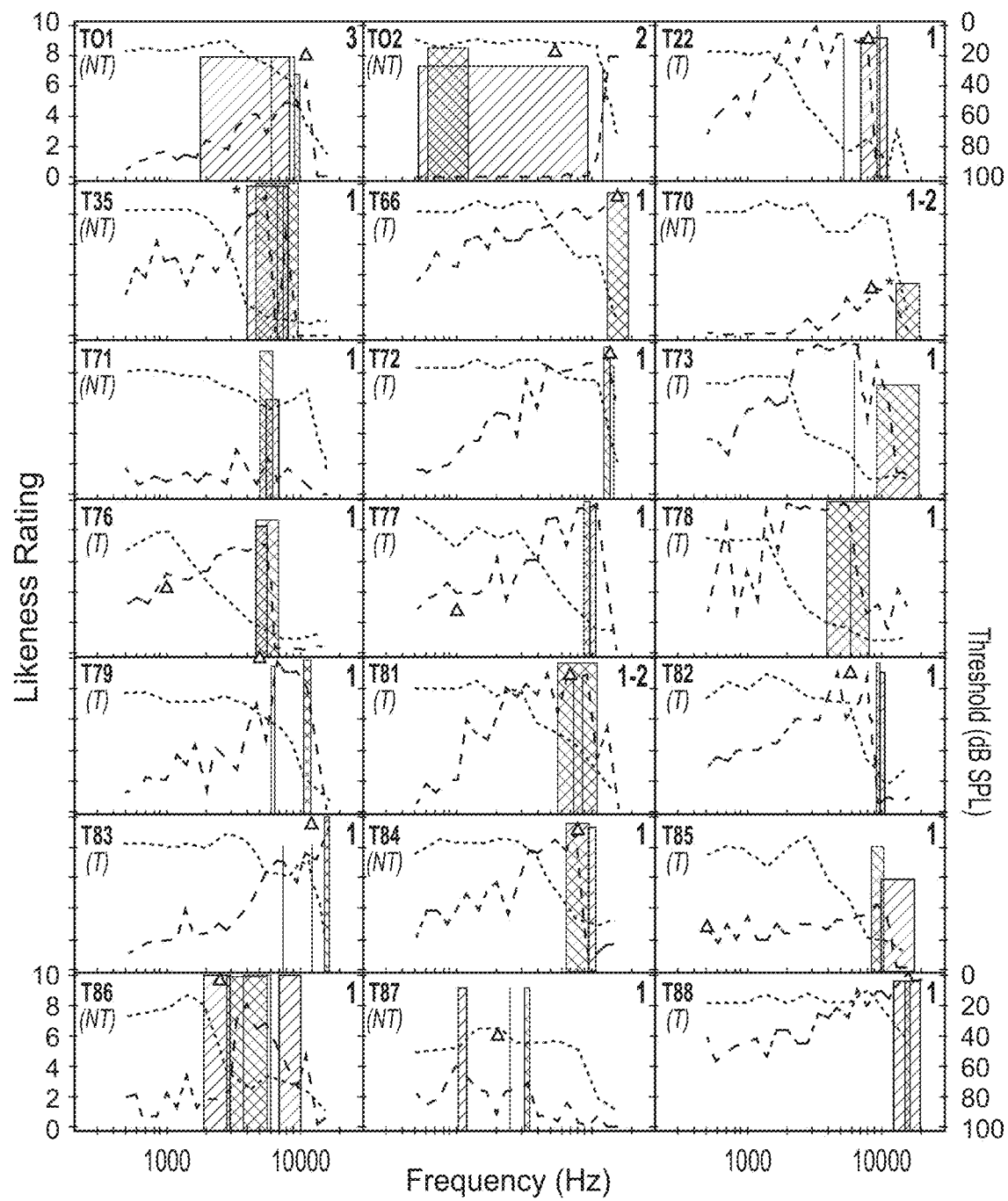
FIG. 11 are plots of tinnitus matching results from individual tinnitus subjects (n=21). Results from tinnitus matching procedures are shown here for individual subjects. Tinnitus spectra (dashed line; as in Norena et al., 2002) indicating likeness ratings [0-10] of pure tones at given CFs from the Adaptive Procedure are shown. The best noise match from the Adaptive Procedure 63 is shown (area filled with crossed lines). The matched component(s) from the Adjustment Procedure are shown (noise components in area filled with parallel lines; pure tone components in the lines bounding the area filled with parallel lines). Rating data for the Adjustment procedure was not available for T35 and T70 (indicated by an asterisk), so levels comparable to the adaptive noise match were used. Results from the "Classic" procedure are shown (open triangles). Subject thresholds (dotted line) are shown in dB SPL (right Y-axis). Subject numbers are listed in the upper left-hand corner of each panel, below which tinnitus classification is listed as tonal (T) or non-tonal (NT). The number of sound components reported by the subject is reported in the upper right corner. Note that thresholds for T01 and T02 shown here are for the non-implanted ear, contralateral to the ear with tinnitus.

FIG. 11 shows individual tinnitus likeness ratings (n=21; different panels) of the resulting tinnitus matches from each of the three methods. In each panel, the individual subject classified their tinnitus as "tonal" or "non-tonal" (the upper left corner), with the number of discrete sound components listed in the upper right corner; see Appendix B for raw data. Audiometric thresholds at frequencies from 500 to 16000 Hz are shown in dotted lines, while the tinnitus spectrum derived from the adaptive tone rankings are shown as a dashed line. The adaptive noise match is represented as a band of noise (cross filled area), while the adjustment method is represented in the parallel line filled area and the bounding lines. The best matched pure tone with the "Classic" method is represented as an open triangle.

There is a great individual variability between subjects as well as between different methods within subjects. Subject T01, for example, is a subject who describes his tinnitus as non-tonal. He describes his "baseline" tinnitus as a white noise, with two pure tone components embedded within it. Accordingly, via the flexible adjustment method (parallel line filled area, with bounding lines), he matches a wide band of noise spanning 1.8-8.4 kHz, with pure tone components at 6 kHz and 9.2 kHz, and ranks the overall adjustment match a 7.8 (of 10). Correspondingly, the best match from the adaptive noise procedure (cross filled area) is a narrowband sound (0.0625-octave bandwidth) around a center frequency of 9514 Hz, which he ranks at a 6.7. The adaptive tone match produces a tinnitus spectrum (dashed line) based on rankings of pure tones at different frequencies, which peaks at 11314 Hz at a 6.1 ranking. The best pure tone from the "classic" match is an 11000 Hz tone (open triangle), which he ranks at an 8.0. He also points out a caveat that his rankings for the "Classic" and adaptive methods is based solely on the pure-tone component of this tinnitus, as none of these sounds resemble the baseline white noise component of his tinnitus.

Introduction of bandwidth (versus sole pure-tone matching) improves the tinnitus match as judged by the subject. In a population of self-described tonal (62%) and non-tonal (38%) tinnitus subjects, the best tinnitus likeness ratings are achieved with the adaptive noise match method. All but one of 21 subjects (95%; n=20) ranked the adaptive noise higher than or equal to the highest-ranked pure tone (adaptive tone match) from the same tinnitus matching method. Two subjects (10%), T78 and T84, ranked their best adaptive noise match equal in similarity to their tinnitus as their best adaptive tone match. Only a single subject (5%; T73) ranked a pure tone higher than a non-pure tone sound. An independent samples t-test showed that the tinnitus likeness ratings using the best adaptive tone match were significantly lower for subjects with non-tonal tinnitus (6.4±2.8), versus those with tonal-type tinnitus (8.9±1.6); t(9.812)=2.311, p=0.044.

Figure 12:
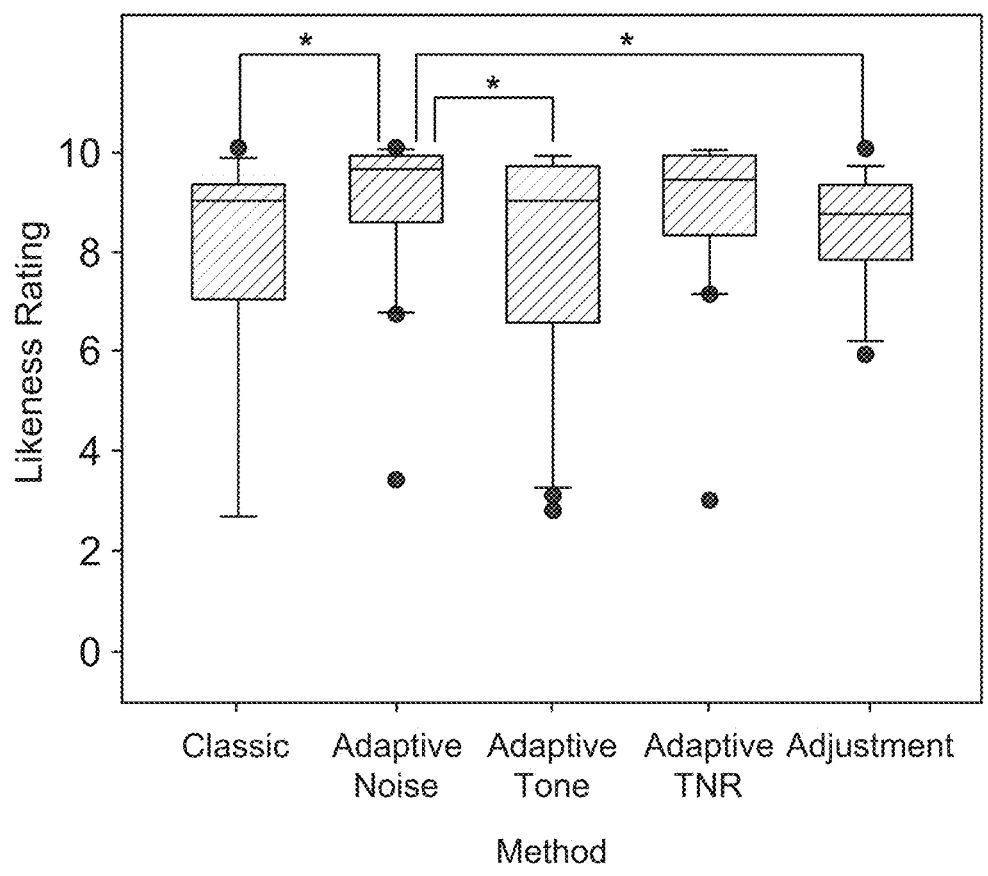
FIG. 12 shows box-plots depicting tinnitus likeness ratings for each method. Statistical significance bars show results of the post-hoc Wilcoxon Signed-Rank Test comparing methods; an asterisk indicates significance of $p<0.05$.

The same improvement in tinnitus likeness rankings associated with the incorporation of the bandwidth component was reflected in the averaged group data. Tinnitus likeness ratings of the tinnitus matched outcomes were compared across methods (FIG. 12). There was a statistically significant difference in the tinnitus likeness ratings across methods, $\chi_2(4)=19.3$, p=0.001 (Friedman test). Median ratings were highest for the adaptive noise match (9.7); mixing in the tone component in the mixed tone-in-noise sound from the adaptive match did not provide statistically higher rankings (9.4), per post-hoc analyses with Wilcoxon Signed-Rank Tests (Z=−1.080, p=0.280). The ratings of the adaptive noise match were statistically higher than those of the adjustment method (9.1; Z=−2.593, p=0.010), adaptive tone match (9.0; Z=−3.185, p=0.001), and "Classic" match (9.0; Z=−2.226, p=0.026). The likeness ratings from the latter three methods were not statistically different from each other.

While many subjects were able to achieve fair matches with pure-tone methods, a subset of subjects did find clear benefit in the tinnitus with the addition of the bandwidth dimension of the matching sound. From the pure-tone matching procedures, 30% (5 of 17) subjects ranked their "Classic" pure tone match at a 7 or less. Subjects T70, T76, T77, T85 and T87 ranked their "Classic" matches at 3.0, 4.2, 2.7, 2.7 and 6.1 respectively; CFs from these matches were much lower in frequency than those matched from the other procedures. Similarly, 29% (6 of 21) subjects ranked their best adaptive tone match at a 7 or less (T01, T70, T71, T76, T85 and T87). Upon incorporation of bandwidth into the tinnitus match, only 10% (2 of 21) subjects of the adaptive noise match (T01 and T70) and 11% (2 of 19) subjects of the adjustment match (T71 and T85) ranked the likeness of the tinnitus match at 7 or less.

The benefit of the bandwidth dimension is clearly illustrated in subject T71, who reports noise like tinnitus. The highest pure-tone ranking he achieves is a 2.8 ranking (3364 Hz); he also ranks a 2.4 ranking (5657 Hz). When bandwidths are introduced, he achieves a 9.3 ranking to a sound centered at 5657 Hz, 0.25-octave bandwidth with the adaptive noise procedure. He matches a nearly-identical sound via the adjustment procedure, selecting a sound centered at 6100 Hz, 0.30-octave bandwidth, which he ranks a 6.2. Likewise, subjects T85, 86 and 87 clearly show similar effects. Despite T85 reporting his sound as tonal, he describes his tinnitus as a "sand or static like sound" and matches his tinnitus to a noise band of sound centered around a high frequency 9.5-13 kHz. Matches to pure tones remain uniformly low at rankings ranging from 2-4 for the adaptive tone match, and his "Classic" match concludes prematurely at 500 Hz, with a low likeness rating at 2.7. T86 describes his tinnitus as a "white noise" and accordingly matches a perfect 10—rated wideband sound ranging from 1.9-10 kHz. T87 describes her tinnitus as "machine noise," and ranks the noise-band sounds at 9.2 levels for both the adaptive noise and adjustment sounds, while her pure-tone matches are ranked lower at 3.9 and 6.1 for the adjustment tone and "Classic" tinnitus matches, respectively.

Figure 13:
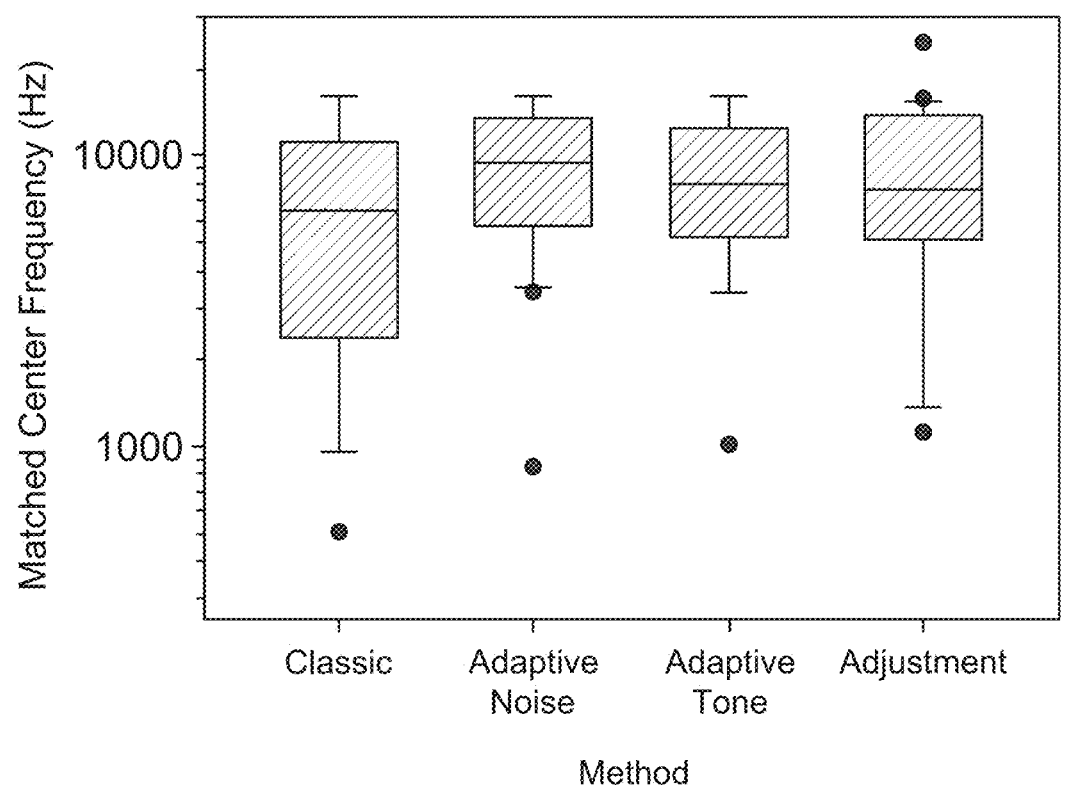
FIG. 13 shows box-plots representing the matched CFs of 21 subjects using the different methods. The top and bottom of the box represents the $25_{th}$ and $75_{th}$ percentile; while the band through the box is at $50_{th}$ percentile. Filled circles represent outliers of this distribution. From left to right, results are. shown for: the "Classic" procedure, the best noise and best tone matches from adaptive procedure, and the adjustment procedure.

Acoustic Characteristics of Tinnitus Pitch Matches. Geometric means of the CFs are shown by methods in FIG. 13. The "Classic" procedure yielded the lowest mean CFs at 4856 Hz. The adaptive procedure yielded mean CFs of 8000 Hz and 7246 Hz for the best matched noise and tone components, respectively; while the adjustment procedure yielded a mean CF of 6977 Hz. No significant differences in CFs were noted between methods in a repeated measures ANOVA analysis on log-transformed CFs.

Figure 14:
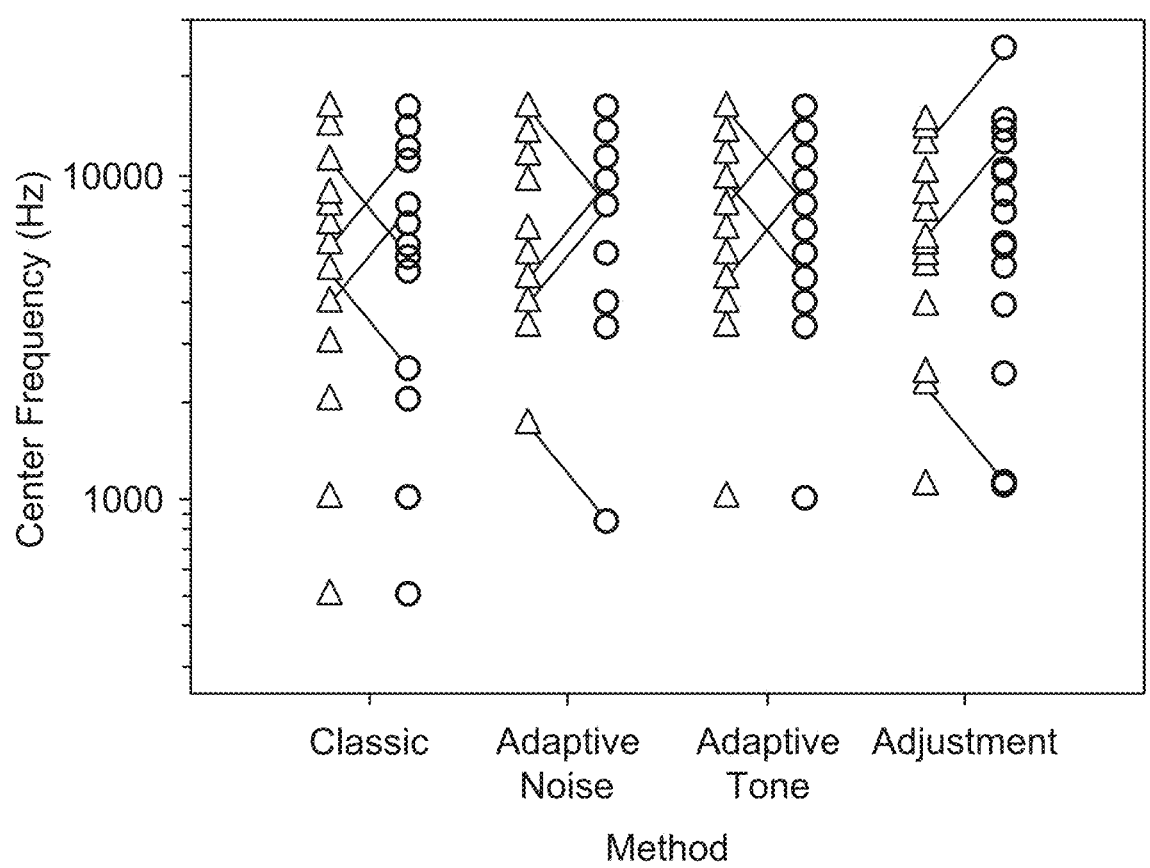
FIG. 14 shows octave verification adjustments, by method. CFs of the original tinnitus match (triangles) are shown alongside the final CFs following octave verification (open circles) for each method. The line connects the original and final CF of the tinnitus match indicates if octave adjustments to a higher or lower octave made (matches to the original octave were not shown for better clarity).

Results from the octave verification step are shown by methods in FIG. 14. Gray triangles represent the original match at the conclusion of the tinnitus matching procedure; open circles represent the matched sound following octave verification step. For individuals who chose the octave-lower or octave-higher sound as their final match, dotted lines connecting the original and final CFs of the tinnitus matches are shown. Approximately equal numbers of octave-higher and octave-lower adjustments were made for each method overall. The "Classic" procedure yielded n=4 octave adjustments, with 2 adjusting to a higher octave and 2 to a lower octave. The adaptive methods also yielded n=4 octave adjustments, similarly with 2 adjusting to a higher octave and 2 to a lower octave. The adjustment procedure yielded n=3 octave adjustments, with 2 adjusting to a higher octave and 1 to a lower octave.

Comparison of Matched Acoustic Characteristics Between Methods.

Figure 15A:
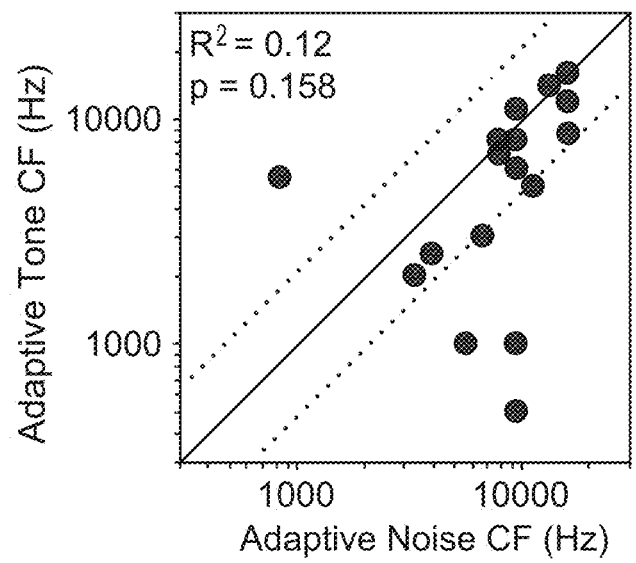
FIGS. 15A-15C are plots of correlation of Center Frequencies (CFs) of methods, compared to adaptive noise CF. CFs from different methods are plotted against CFs from the adaptive tone match here. Pearson correlation coefficients are shown in the upper left corner. The solid line represents the equivalence line between the actual and matched CFs; dotted lines represent CFs corresponding to one-octave above and below the actual CF.
Figure 15B:
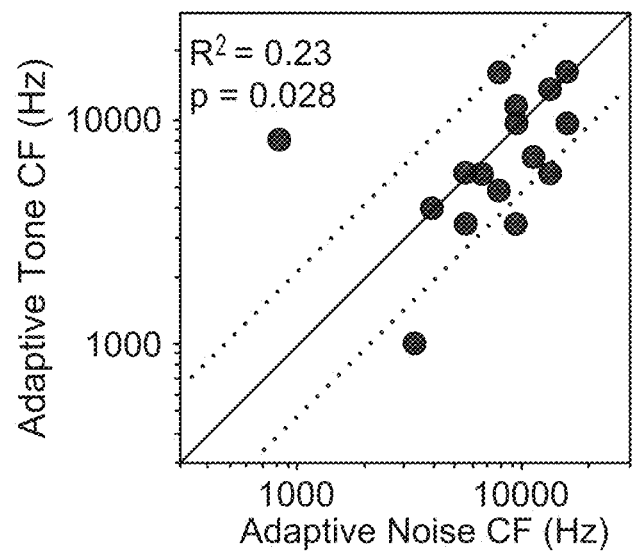
Figure 15C:
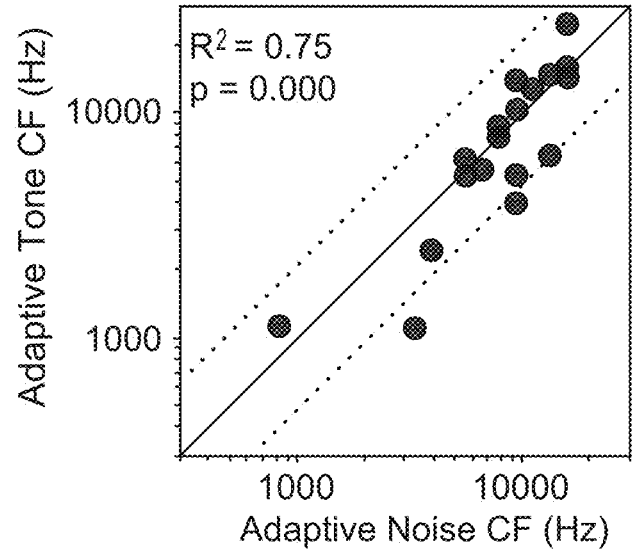

Matched CFs and bandwidths were also evaluated between methods. Correlation plots showing CFs from different methods plotted against CFs from the adaptive noise match are shown in FIGS. 15A-15C. In FIG. 15A, CFs from the "Classic" method are shown against CFs from the adaptive noise match, resulting in a Pearson correlation of $R_2=0.12$, p=0.158. Notably, CFs from the "Classic" procedure tend to be matched at lower frequencies than those from the adaptive noise match; a near-significant difference is found in the CFs between the two methods; t(17)=−2.087, p=0.052 (paired samples t-test). Correlation between the adaptive tone and noise CFs is slightly higher at $R_2=0.23$, p=0.028 (FIG. 15B), while the highest correlation is seen between the adjustment CF and adaptive noise CF, $R_2=0.75$, p=0.000 (FIG. 15C). Correlation between the "Classic" and adaptive tone match was $R_2=0.16$, p=0.096 (not shown). Lastly, low correlation between matched bandwidths from the adaptive noise match and the adjustment procedure were given by a Pearson correlation of $R_2=0.10$, p=0.155.

Time Cost of Tinnitus Matching Procedures.

Figure 16:
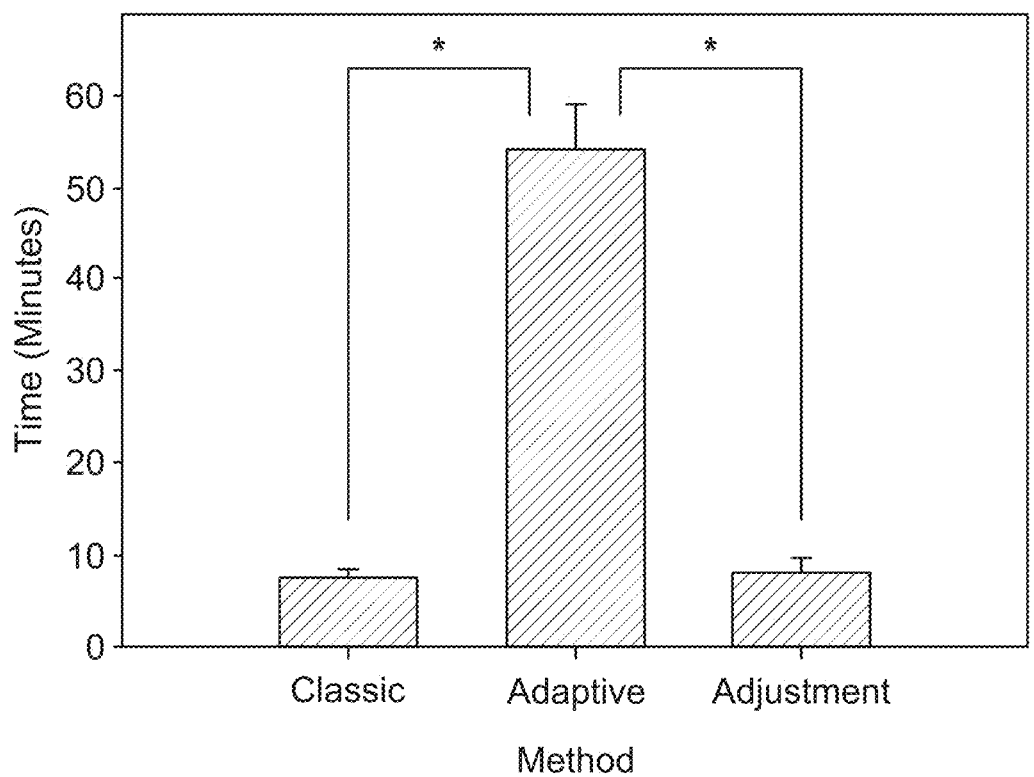
FIG. 16 shows a plot of average time required to complete each procedure is shown here, by method. The height of the bar represents the mean time to completion, while error bars represent standard error. Statistical significance bars show results of post-hoc analysis using the Bonferroni correction; an asterisk indicates significance of $p<0.05$.

Next, efficiency of each method was evaluated (FIG. 16). A repeated-measures ANOVA with Greenhouse-Geisser correction showed the time-costs for these 3 methods to be significantly different (F(1.030, 14.427)=58.204, p=0.000). Post-hoc analyses using the Bonferroni correction showed that Adaptive method was significantly longer than the "Classic" and Adjustment procedures (p<0.001), but there was no significant difference between the "Classic" and Adjustment procedures (p=0.866). The "Classic" procedure and Adjustment procedures were completed in 7.6±3.6 minutes (mean±SD) and 8.0±7.7 minutes, respectively, while the Adaptive procedure took 54.1±4.9 minutes.

Improvement of Tinnitus Matching with Incorporation of Bandwidth.

Figure 17:
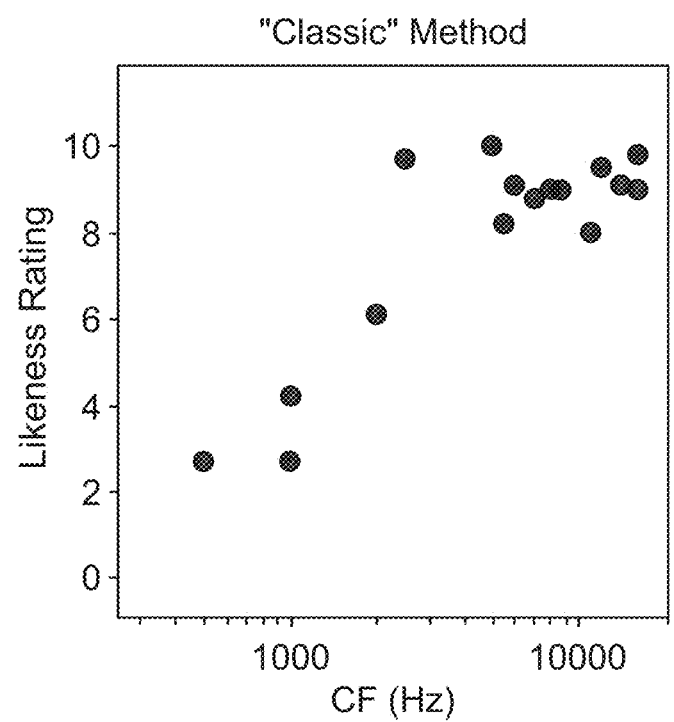
FIG. 17 is a plot of tinnitus likeness rating by CF, for the "Classic" method

The primary aim of this study was to improve upon current tinnitus matching techniques in order to better match the documented complexities of tinnitus. From our study population, roughly a quarter (24%; 4 of 17 subjects) of these subjects is unable to obtain a satisfactory tinnitus match (7+ rating) with the "Classic" method (FIG. 17); a fifth subject (T01) indicates that his 8.0 ranking corresponded to only the pure tone-component of his tinnitus as the pure tones were "too different" from his baseline white-noise tinnitus component for him to compare. Several subjects also terminated the procedure prematurely, therefore matching to a lower frequency sound at a low ranking. CFs matched with the "Classic" procedure also tended to be lower than CFs when sounds are presented randomly (FIG. 15A), likely due to the ascending nature of this procedure (the procedure begins from 1000 Hz and concludes when a reversal is made; namely that the lower of the two presented frequencies is selected as being closer to the tinnitus).

The addition of bandwidth into tinnitus matching provides significantly higher tinnitus likeness ratings for our study population as compared to the two pure tone-based matching methods tested here. Perhaps more significantly, the addition of bandwidth provides a large marginal benefit to a quarter of our subjects who are unable to achieve satisfactory tinnitus matches using pure-tones alone.

Precision of the Tinnitus Match.

Furthermore, subjects achieve a more precise tinnitus match with the incorporation of bandwidth into the tinnitus match. This is indicated by the high degree of correlation between matched CFs between the adaptive noise and adjustment procedures ($R_2=0.75$) versus the low correlation between the "Classic" and adaptive tone procedures ($R_2=0.16$). While the accuracy of tinnitus matching cannot be ascertained without an objective or even "gold standard" measurement method, normal hearing subjects are able to match simulated tinnitus sounds with higher accuracy when bandwidth is considered (correlation to the actual tinnitus sound is $R_2=0.97$ and 0.87) versus matching to conventional pure tones ($R_2=0.80$ for the adaptive tone method).

Time Cost.

For practical purposes, time cost and delivery of these procedures also need to be considered. The "Classic" and Adjustment procedures were comparable in efficiency, where both were completed in approximately 8 minutes. On the other hand, the adaptive procedure took nearly 5 times as long, with an average 54 minutes to completion. Of particular interest, the adaptive and adjustment are computer-automated programs, where subjects complete the procedures on their own following instructions given by the experimenter. In contrast, the "Classic" procedure requires the experimenter to be present throughout the procedure in order to manually adjust and deliver the matching pure-tones. The computer-automated procedures offer two distinct advantages: 1) elimination of experimenter-dependent bias or variability, and 2) time-efficiency for the clinician or experimenter.

Flexibility of adjustment procedure to match complex tinnitus. Lastly, the adjustment procedure offers a distinct advantage in the option to incorporate additional sound components into the tinnitus match. Subjects who have complex tinnitus (e.g. 2 or more sounds) can derive benefit from the option of adding multiple components, whether the sounds are noise or pure tones. Nearly half (48%; 10 of 21 subjects) matched more than one component to their tinnitus, while 2 of these subjects matched 3 components. Distinctly, subject T01 reported a baseline white-noise component, with two distinct pure tones in his tinnitus and accordingly matched 3 components resembling his description (see detailed description in Results). Similarly, subject T02 reports a complex tinnitus with two sound components—a white noise background with an additional pure tone. She matches with the adjustment method to a wide-band noise spanning 500 to 9500 Hz, along with a pure tone at 12500 Hz. Again, the best adaptive tone match at 16000 Hz corresponds to the pure tone component of the adjustment method, but does not sufficiently represent the described "white noise" component of her tinnitus. For these subjects, the pure tone matches from the "Classic" and adaptive tone procedures are able to approximate the pure tone components of the described tinnitus. However, the adjustment method affords these subjects the bandwidth control to better reproduce the described "white noise" components, while allowing them to add in additional pure tone noise components.

Conclusions

Here we present the results from three tinnitus matching methods: a thorough, controlled and fully randomized "Adaptive" procedure; a flexible, user-controlled "Adjustment" method; and a "Classic" procedure based on previous methods developed by Vernon and Meikle (1988). While nearly all available tinnitus matching procedures use pure-tones to match tinnitus, we show here that pure tones are not sufficient to match a given subset of tinnitus subjects (~30% of tinnitus subjects rank <7 of 10 using the "Classic" match). The additional dimension of bandwidth to the tinnitus matching procedure significantly increases tinnitus matches as measured by tinnitus likeness ratings. Additionally, a relatively high degree of correlation of matched CF between the adaptive and adjustment methods ($R_2=0.75$) is indicative of the precision achieved when incorporating bandwidth into the tinnitus match. When considering the high likeness rankings for the outcomes of each procedure (9.7 and 9.1 of 10 for the adaptive noise and adjustment methods, respectively), along with the time cost (54 min and 8 min, respectively), we recommend the adjustment procedure as an efficient method to incorporate bandwidth into the tinnitus match for improved outcomes, in order to improve upon currently available tinnitus matching methods.

New Procedure

Figure 18:
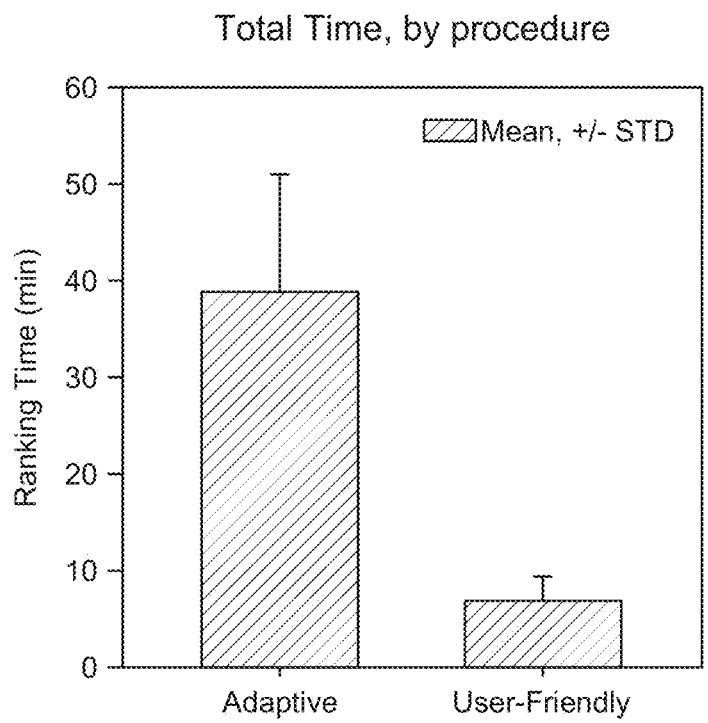
FIG. 18 is a plot of total time of two procedures.

In order to compare the time efficiency of the two procedures, the average time of the adaptive procedure (39.0±12.0 minutes) over 7 tinnitus patients is compared to that of the user-friendly procedure (6.6±2.5 minutes) in FIG. 18. In conclusion, the time of the user-friendly procedure significantly drops 491%.

In regard to the outcomes of the adaptive procedure, they are 1) the predominate center frequency (CF); 2) the bandwidth (BW) of the narrow band noise; 3) the pure tone-to-noise (TNR); 4) the equal loudness (EL) in dB SPL; and 5) the threshold (THR) in dB SPL/Therefore the matched sound can be characterized by a joint vector [CF, BW, TNR, EL, and THR].

We do not distinguish narrow-band noises (with bandwidth larger than 0.1 octave) from very narrowband noises (with bandwidth less than 0.1 octave), although the two kinds sound quite different in quality by human subjects. Furthermore, very narrowband noises have required us to develop special signal processing (SP) techniques to generate them due to their unique characteristics. The SP techniques are different from what is commonly used to generate narrowband noises. For convenience, when narrow-band noises are mentioned, it includes both kinds.

The procedure is to systematically search a parameter space for a best match out of tens of thousands of candidate sounds. The outcomes also need to better represent the perception of one's tinnitus in a reliable and unbiased manner.

The procedure will further research efforts into classifying patients regarding types of tinnitus, its origin, and best treatment option(s), thus continuing to advance the field of tinnitus research. Particularly, the result [CF, BW, TNR, EL, and THR] can be employed as an input vector of an artificial neural network (ANN) to predict and recommend the most effective treatment option. The vector may be further combined with audiograms, DPOAEs, and other necessary clinical measures.

Figure 19:
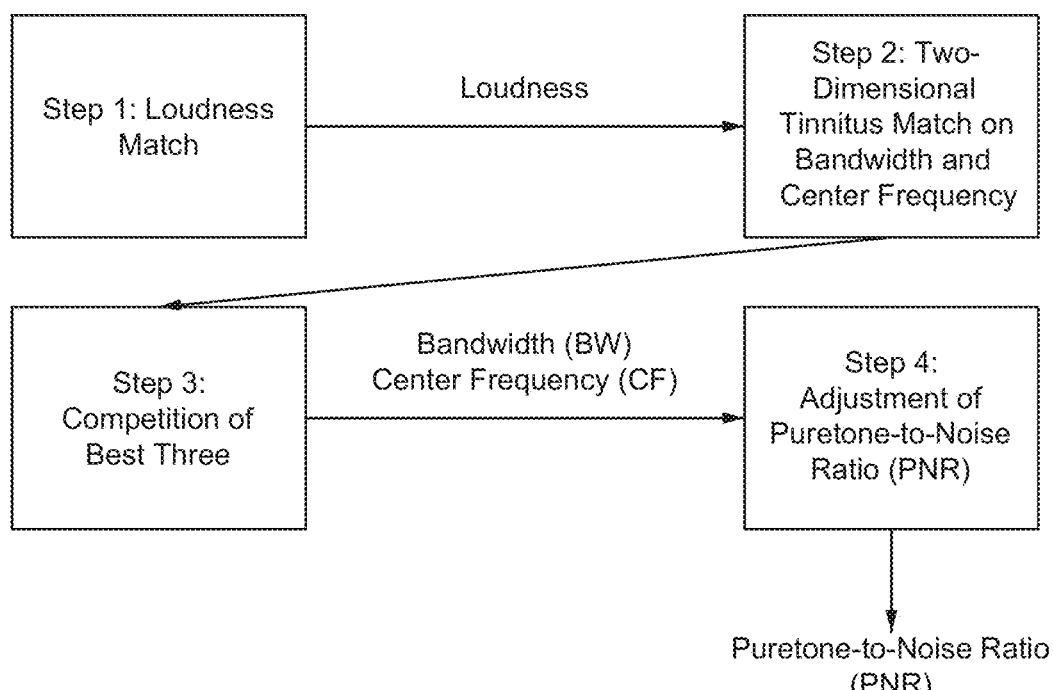
FIG. 19 illustrates four steps of an adaptive procedure, according to an embodiments.

The tinnitus will be matched by having an individual listen to different sounds routed through earphones or headphones. It can be directed by a clinician or can be self-direct by the patient on a hand-held device, a standalone computer, or from an online website to search for the optimized match, it is important that subjects have as much perceptual separation as possible between the external stimulus and the perceived tinnitus. Therefore, subjects will be asked to match their tinnitus in the loudest ear to sounds delivered to the contralateral ear. Should the individual's report equal loudness between ears, or should the tinnitus be perceived in the head at midline, then the better hearing ear will be chosen. FIG. 19 is a diagram of how the spectrum match will take place in four steps.

The purpose is to develop an accurate means of identifying the tinnitus spectrum heard by an individual suffering from tinnitus. Accurate match is necessary to further understand the underlying mechanisms of tinnitus, to generate customized sound therapy, and to predict the success of treatment options. Currently, most sound therapies achieve tinnitus suppression by targeting the tinnitus frequency region. Therefore, it is very important to achieve an accurate tinnitus match. No tinnitus therapy is 100% successful and the failures may be related to miss-targeting frequencies or not targeting enough frequencies.

The Table 3 below highlights 4 subjects that were pitch matched using the clinical standard pure tones and by our adaptive procedure. Subjects were asked to rank on a scale between 0 and 10 how similar the external tone was to their tinnitus (0=no match; 10=perfect match). In all cases, our invention generated a sound that much better matched the individual tinnitus. In subject 3 (S3), the tinnitus spectrum was then manipulated and played back to the patient, resulting in strong tinnitus suppression. An additional note was that this subject (S3) didn't derive any tinnitus suppression using amplitude modulation with the pitch-matched pure tone carrier.

TABLE 3

Comparison between Clinical Standard and the Adaptive Procedure

|  | Clinical Gold Standard | The Adaptive Procedure |
|---|---|---|
| S1 | 7 | 10 |
| S2 | 2 | 6 |
| S3 | 4 | 8* |
| S4 | 3 | 9 |

*The tinnitus is treated by the matched sound for 3 minutes resulting is strong suppression The Table 3 below highlights 4 subjects that were pitch matched using the clinical standard pure tones and by our adaptive procedure. Subjects were asked to rank on a scale between 0 and 10 how similar the external tone was to their tinnitus (0=no match; 10=perfect match). In all cases, our invention generated a sound that much better matched the individual tinnitus. In subject 3 (S3), the tinnitus spectrum was then manipulated and played back to the patient, resulting in strong tinnitus suppression. An additional note was that this subject (S3) didn't derive any tinnitus suppression using amplitude modulation with the pitch-matched pure tone carrier.

User Friendly Procedure

The user-friendly procedure is designed as shown in FIG. 7. Two triangles on the first panel are the low and high cutoffs of the synthesized sound, while the volume bar is adjustable on the right. For a user-friendly (UF) procedure, 24 normal hearing subjects have been recruited to test it. The 24 subjects are randomly divided into three groups: a pure-tone group, a noise group, and a tone-in noise group. Eight subjects are given a pure-tone on one ear and instructed to adjust the quality of a contralateral sound to match the pure-tone. The level, the low cutoff frequency, and the high cutoff frequency can be freely adjusted to match the target sound. Another eight subjects are given a noise. The remaining eight subjects are given a tone in noise. The subjects may open a second window or a third one if there are more appreciable components in his tinnitus.

Figure 20:
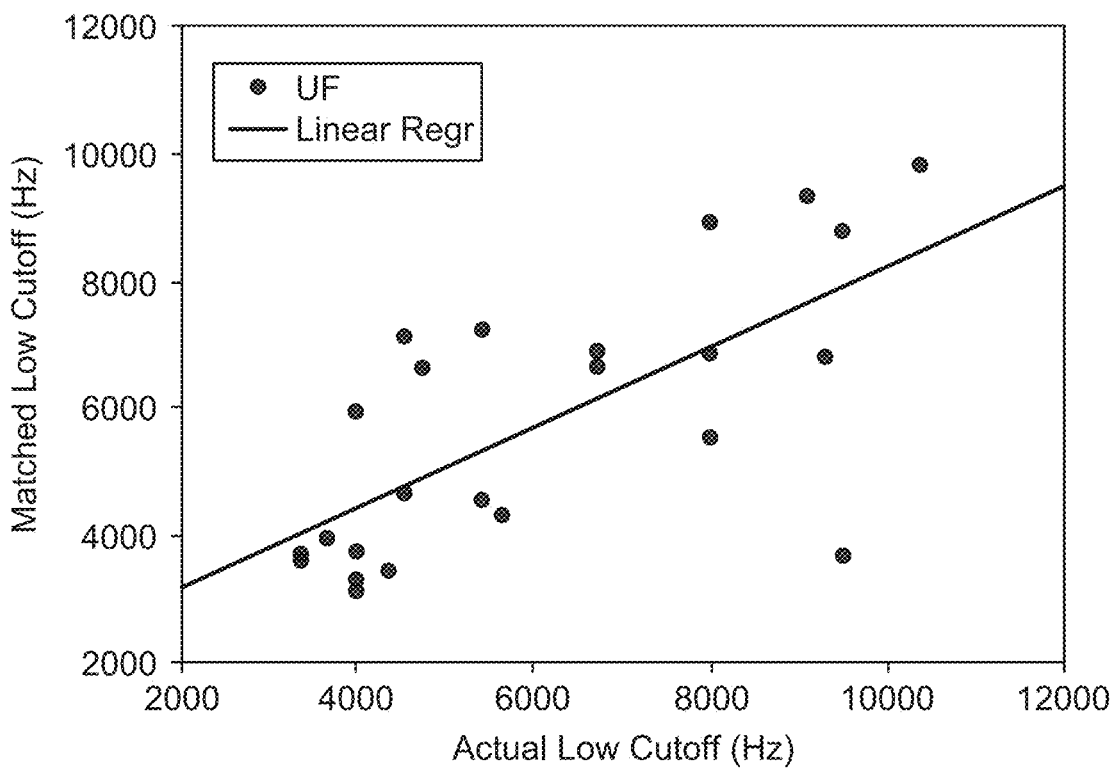
FIG. 20 is a scatter-plot of normal hearing data for 25 subjects.

Test Results:

there exists a significant correlation ($p<0.01$, $r=0.63$) between the low cutoff of an actual sound (that simulates tinnitus) and the low cutoff of a matched sound (see FIG. 20). The statistical conclusion comes when: (1) all data of 24 subjects are included, and (2) an octave adjustment of six subjects is done as follows (see Table 4):

TABLE 4

| Subject ID | Actual low cutoff (Hz) | UF-matched low cutoff (Hz) | Adjusted low cutoff (to either one octave higher or lower) |
|---|---|---|---|
| 7 | 9111 | 4641 | 9282 |
| 9 | 10375 | 4883 | 9766 |
| 14 | 4555 | 2311 | 4622 |
| 15 | 5417 | 14385 | 7193 |
| 17 | 4757 | 13237 | 6619 |
| 19 | 4000 | 6561 | 3281 |

Figure 21:
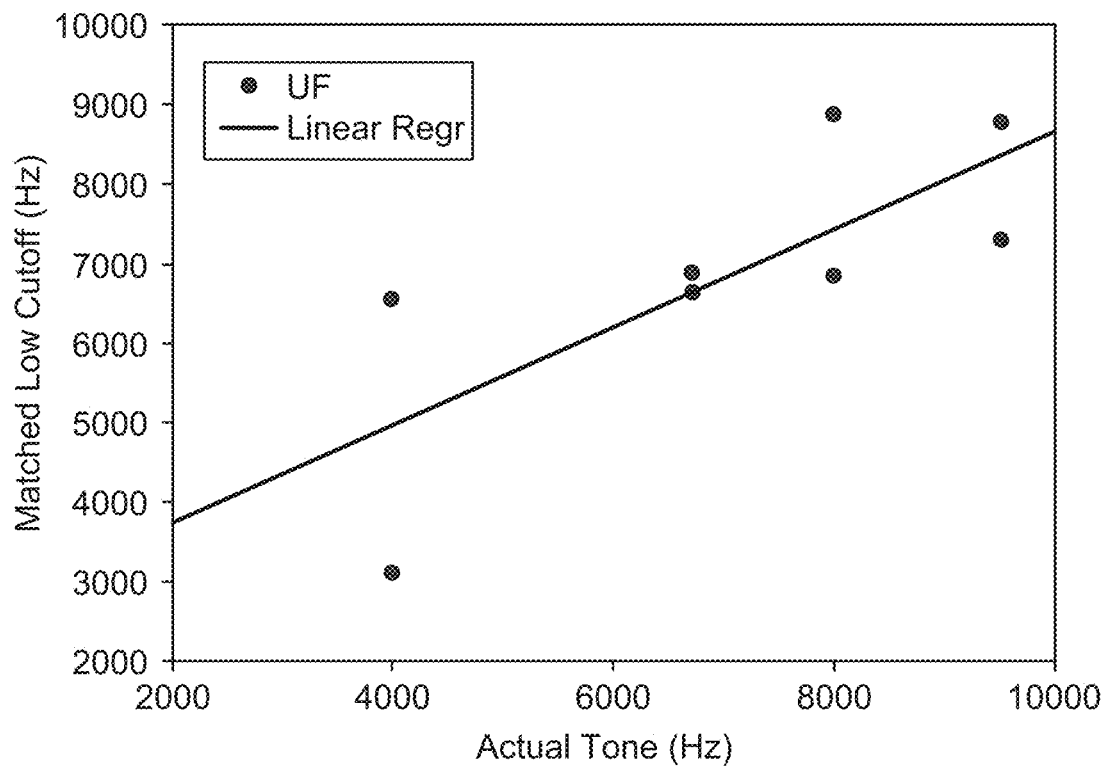
FIG. 21 is a scatter-plot of normal hearing data for 8 subjects in a pure-tone group.

In regard to the matched sounds of 8 subjects in the pure-tone group, there also exists a significant correlation ($p<0.05$, $r=0.74$) between the actual pure-tone frequency and the low cutoff of the matched sound (see FIG. 21). The significant correlation comes with the 8 subjects of the pure-tone group. Additionally, the octave adjustment is done on one subject (see Table 5):

TABLE 5

| Subject ID | Actual low cutoff (Hz) | UF-matched low cutoff (Hz) | Adjusted low cutoff (to either one octave higher or lower) |
|---|---|---|---|
| 8 | 9514 | 3633 | 7266** |

**Even if a pure-tone was actually presented, a subject may match to a narrow band noise.

The above results suggest that the user-friendly procedure, once adjusted for octave illusion, can be a reliable method to match an external sound to tinnitus.

Test/Re-Test Reliability

Figure 22A:
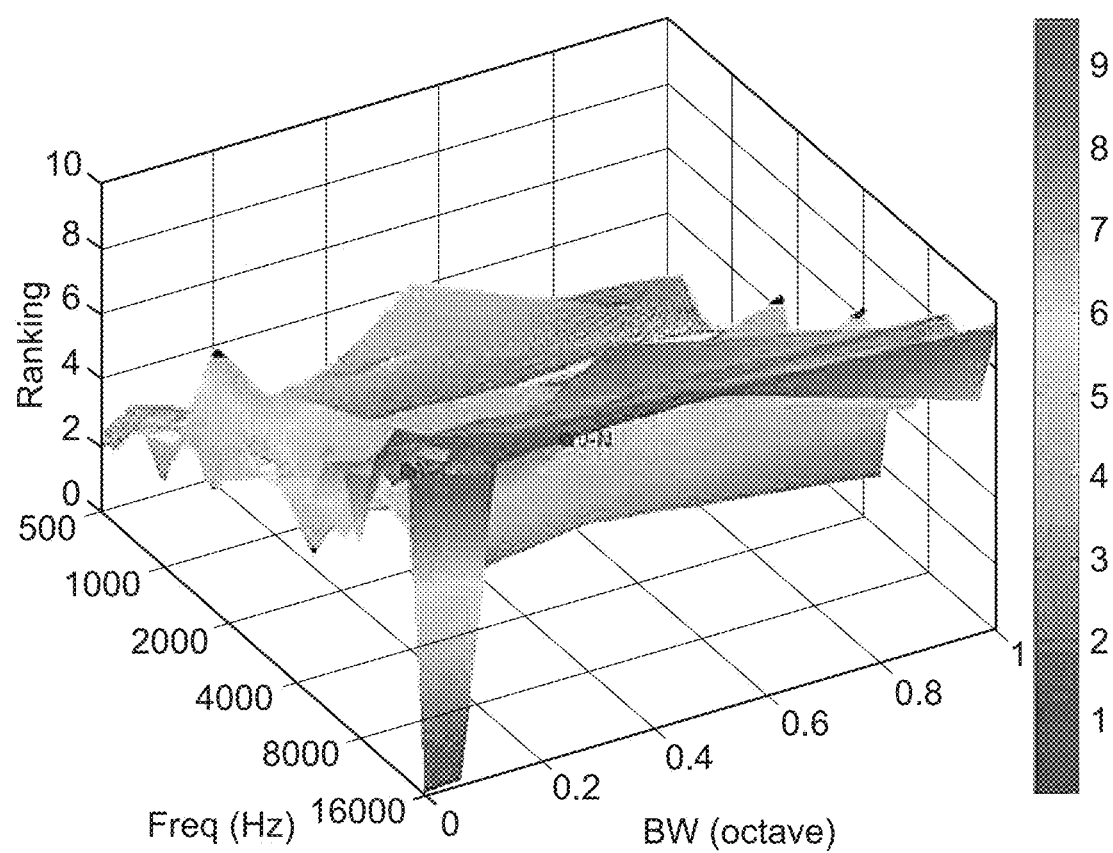
FIGS. 22A-22C are plots of different repetitions of an adaptive procedure.
Figure 22B:
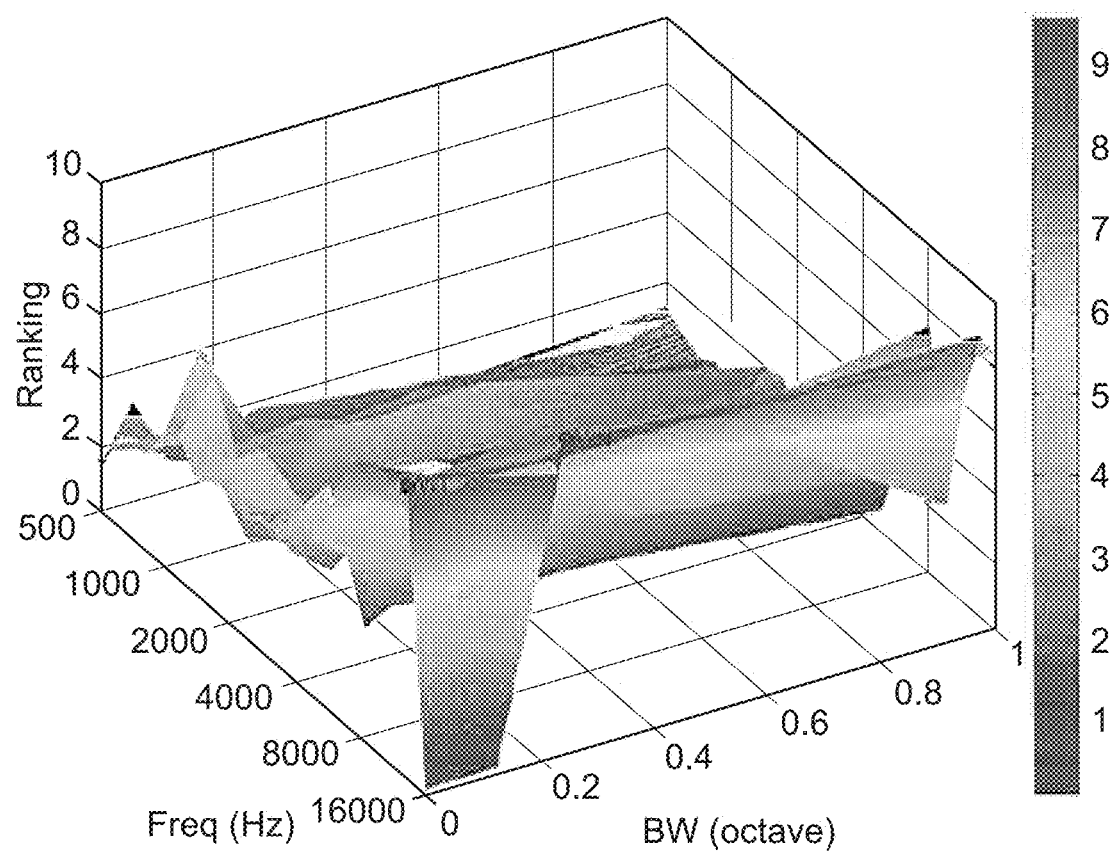
Figure 22C:
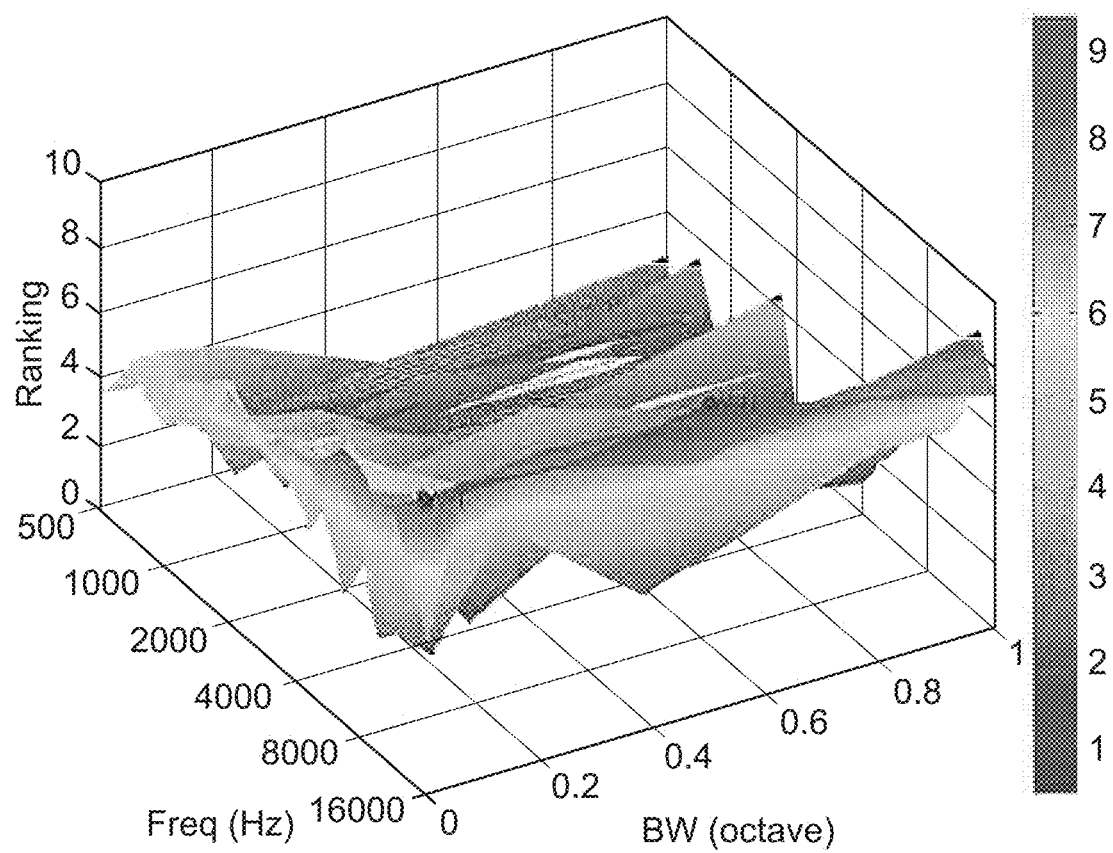

Adaptive Procedure:

In order to verify test/re-test reliability, FIGS. 22A-22C illustrate three repetitions of the adaptive procedure on one tinnitus patient. Based on the figures, the repeated measures hold reliable for both the matched noise and the matched pure-tone. See also Table 6.

TABLE 6

Three Repetitions of Adaptive Procedure

| | Best Matched Noise | | | Best Matched Pure-tone | |
|---|---|---|---|---|---|
| Measure # | Center Frequency (Hz) | Bandwidth (octave) | Rank on Similarity (0-10) | Frequency (Hz) | Rank on Similarity (0-10) |
| 1 | 16000 | .25 | 9.6 | 13454 | 9.5 |
| 2 | 16000 | .25 | 9.6 | 13454 | 9.0 |
| 2 | 16000 | .50 | 9.4 | 16000 | 9.0 |

Figure 23A:
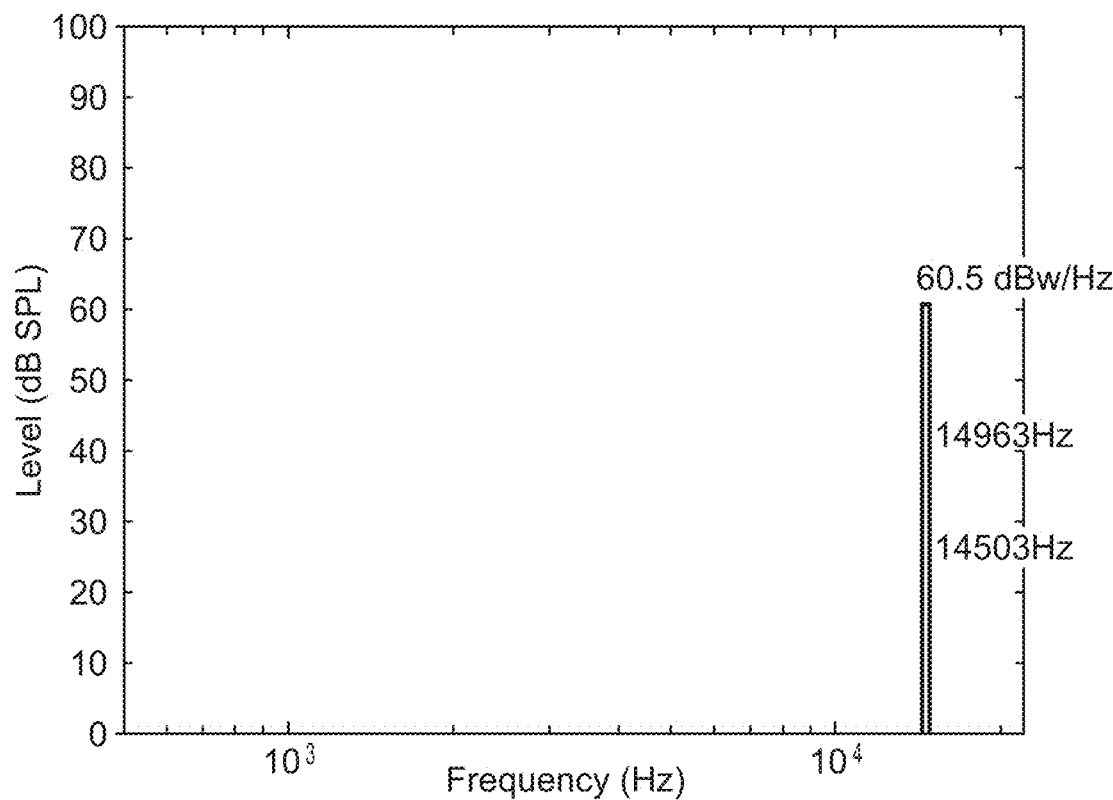
FIGS. 23A-23C are plots of different repetitions of a user-friendly procedure.
Figure 23B:
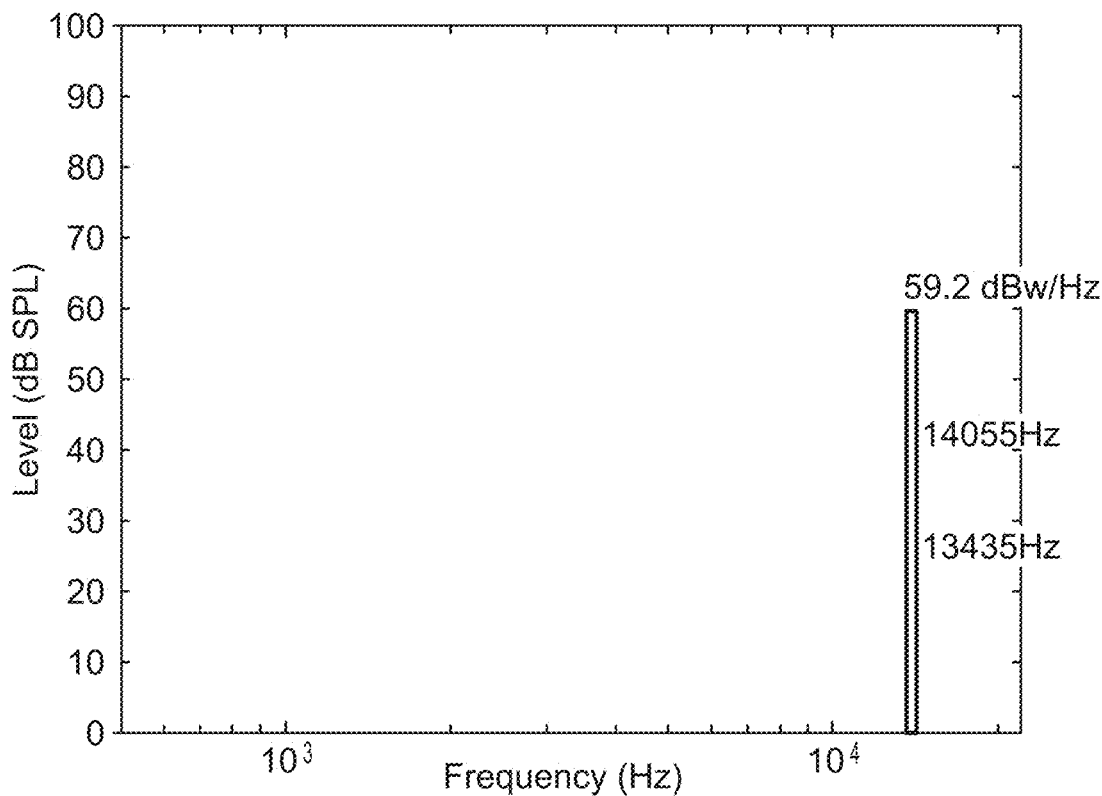
Figure 23C:
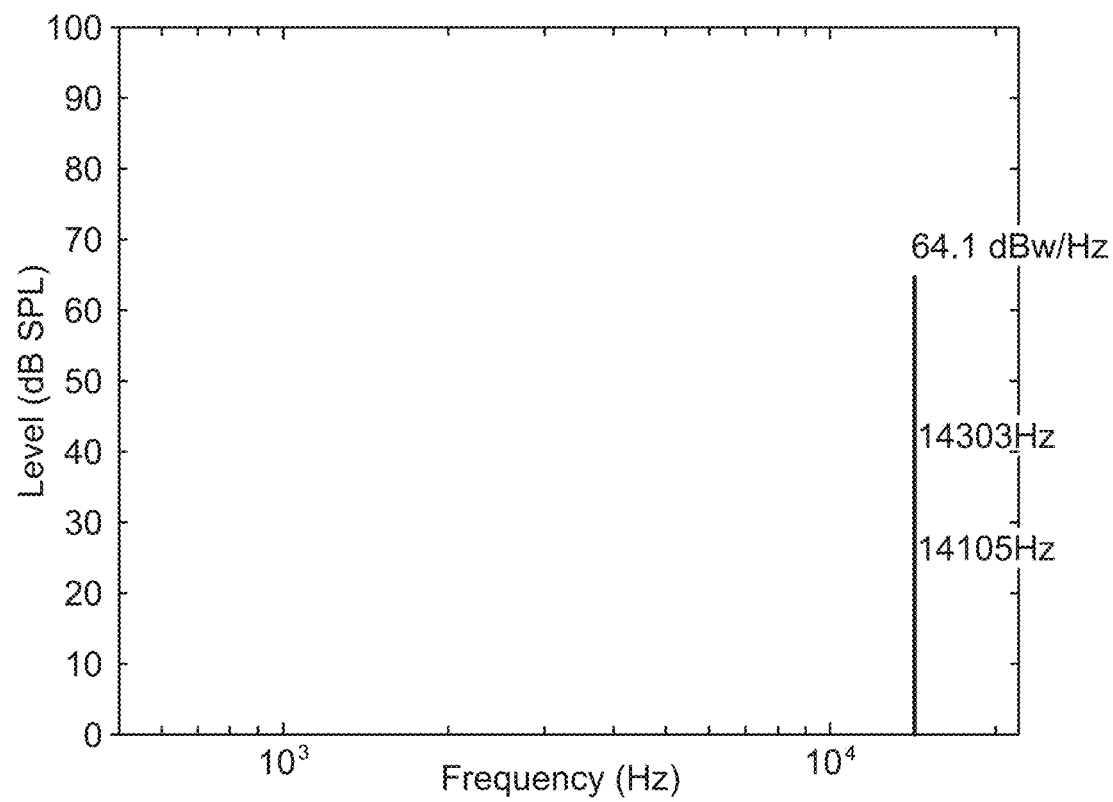

User Friendly Procedure:

FIGS. 23A-23C give three repetitions of the user-friendly procedure on one tinnitus patient. Based on the figures, the repeated measures also hold reliable. See also Table 7.

TABLE 7

Three Repetitions of User Friendly Procedure

| | Best Matched Sound | | |
|---|---|---|---|
| Measure # | Low Cutoff (Hz) | High Cutoff (Hz) | Rank on Similarity (0-10) |
| 1 | 14503 | 14963 | 8.4 |
| 2 | 13435 | 14055 | 8.4 |
| 2 | 14105 | 14303 | 8.6 |

There are a few advantages to this invention over clinically based methods for tinnitus pitch matching. The advantages include: (1) Fast (6.6±2.5 minutes), (2) Accurate (patients report highly similar, near perfect matches), (3) Reliable (patients repeat the procedures and obtain the same matches), (4) Automated (no bias of experimenter), (5) Constructing an individualized sound for sound therapy or tinnitus suppression, (6) Portable (the procedures can be accomplished in clinic or at home), and (7) Predicting treatment outcomes through an artificial neural network.

TABLE A

Sound Stimuli Available for Tinnitus Match (n = 127)

| | | 6 BWs | | | | | |
|---|---|---|---|---|---|---|---|
| | CF/BW | 0 | 0.0625 | 0.125 | 0.25 | 0.5 | 1 octave |
| 21CFs | 500 Hz | 500, 500 | 489, 511 | 479, 522 | 459, 545 | 420, 595 | 354, 707 |
| | 595 Hz | 595, 595 | 582, 608 | 569, 621 | 545, 648 | 500, 707 | 420, 841 |
| | 707 Hz | 707, 707 | 692, 723 | 677, 738 | 648, 711 | 595, 841 | 500, 1000 |
| | 841 Hz | 841, 841 | 823, 859 | 805, 878 | 771, 917 | 707, 1000 | 595, 1189 |
| | 1000 Hz | 1000, 1000 | 979, 1022 | 958, 1044 | 917, 1091 | 841, 1189 | 707, 1414 |
| | 1189 Hz | 1189, 1189 | 1164, 1215 | 1139, 1242 | 1091, 1297 | 1000, 1414 | 341, 1682 |
| | 1414 Hz | 1414, 1414 | 1334, 1445 | 1354, 1477 | 1297, 1542 | 1189, 1682 | 1000, 2000 |
| | 1682 Hz | 1682, 1682 | 1646, 1719 | 1610, 1756 | 1542, 1834 | 1414, 2000 | 1189, 2378 |
| | 2000 Hz | 2000, 2000 | 1957, 2044 | 1915, 2089 | 1834, 2181 | 1682, 2378 | 1414, 2828 |
| | 2378 Hz | 2378, 2378 | 2327, 2430 | 2278, 2484 | 2181, 2594 | 2000, 2828 | 1682, 3364 |
| | 2823 Hz | 2828, 2828 | 2768, 2890 | 2709, 2954 | 2594, 3084 | 2378, 3364 | 2000, 4000 |
| | 3364 Hz | 3364, 3364 | 3292, 3437 | 3221, 3513 | 3084, 3668 | 2828, 4000 | 2378, 4757 |
| | 4000 Hz | 4000, 4000 | 3914, 4088 | 3830, 4177 | 3668, 4362 | 3364, 4757 | 2828, 5657 |
| | 4757 Hz | 4757, 4757 | 4655, 4861 | 4555, 4967 | 4362, 5187 | 4000, 5657 | 3364, 6727 |
| | 5657 Hz | 5657, 5657 | 5536, 5781 | 5417, 5907 | 5187, 6169 | 4757, 6727 | 4000, 8000 |
| | 6727 Hz | 6727, 6727 | 6583, 6874 | 6442, 7025 | 6169, 7336 | 5657, 8000 | 4157, 9514 |
| | 8000 Hz | 8000, 3000 | 7829, 8175 | 7661, 8354 | 7336, 8724 | 6727, 9514 | 5657, 11314 |
| | 9514 Hz | 9514, 9514 | 9310, 9722 | 9110, 9935 | 8724, 10375 | 8000, 11314 | 6727, 13454 |
| | 11314 Hz | 11314, 11314 | 11071, 11561 | 10834, 11815 | 10375, 12338 | 9514, 13454 | 8000, 16000 |
| | 13454 Hz | 13454, 13454 | 13166, 13749 | 12884, 14050 | 12338, 14672 | 11314, 16000 | 9514, 19027 |
| | 16000 Hz | 16000, 16000 | 15657, 16350 | 15322, 16708 | 14672, 17448 | 13454, 19027 | 11314, 22050 |
| | WN | | | | | | {354, 22050} |

TABLE B

Individual Tinnitus Matching Results

| | Adaptive | | | | | | | | | |
|---|---|---|---|---|---|---|---|---|---|---|
| | Classic | | Noise | | | Tone | | WN | TNR | |
| | CF | Rank | CF | BW | Rank | CF | Rank | Rank | TNR | Rank |
| T01 | 11000 | 8 | 9514 | 0.0625 | 6.7 | 11314 | 6.1 | 2.2 | 40 | 7.1 |
| T02 | 5500 | 8.2 | 841 | 1 | 8.5 | 8000 | 8.2 | 4.3 | 40 | 8.3 |
| T22 | 8000 | 9 | 9514 | 0.0625 | 10 | 3364 | 9.9 | 0.5 | −10 | 9.4 |
| T35 | 3000 | n.a. | 6727 | 1 | 10 | 5657 | 9.4 | 3.4 | −30 | 10 |
| T66 | 16000 | 9 | 16000 | 0.5 | 9.4 | 16000 | 9 | 0.4 | −40 | 8 |
| T70 | 8600 | 9 | 16000 | 0.5 | 3.4 | 9514 | 3.1 | 0.1 | −40 | 3 |
| T71 | n.a. | n.a. | 5657 | 0.25 | 9.3 | 3364 | 2.8 | 7.2 | −15 | 8.4 |
| T72 | 14000 | 9.1 | 13454 | 0.125 | 9.6 | 13454 | 9 | 1.4 | 15 | 9.4 |

TABLE B-continued

Individual Tinnitus Matching Results

| | | | | | | | | | | |
|---|---|---|---|---|---|---|---|---|---|---|
| T73 | n.a. | n.a. | 13454 | 1 | 7.1 | 5657 | 9.9 | 5.3 | 40 | 9.2 |
| T76 | 1000 | 4.2 | 5657 | 0.5 | 8.6 | 5657 | 7 | 5.4 | 25 | 9.4 |
| T77 | 1000 | 2.7 | 9514 | 0.125 | 9.9 | 11314 | 9.8 | 0 | 30 | 10 |
| T78 | n.a. | n.a. | 5657 | 1 | 9.9 | 5657 | 9.9 | 0.9 | 20 | 9.8 |
| T79 | 5000 | 10 | 11314 | 0.125 | 9.9 | 6727 | 9.8 | 0.6 | −30 | 10 |
| T81 | 7000 | 8.8 | 8000 | 1 | 9.7 | 4757 | 8.9 | 0.6 | 40 | 8.8 |
| T82 | 6000 | 9.1 | 9514 | 0.0625 | 9.7 | 9514 | 9.1 | 0.5 | 20 | 8.3 |
| T83 | 12000 | 9.5 | 16000 | 0.0625 | 9.9 | 16000 | 9.4 | 0.1 | Inf | 10 |
| T84 | 8000 | 9 | 8000 | 0.5 | 9.5 | 16000 | 9.5 | 8.7 | −35 | 9.3 |
| T85 | 500 | 2.7 | 9514 | 0.25 | 8 | 9514 | 4.3 | 2.8 | 15 | 7.3 |
| T86 | 2500 | 9.7 | 4000 | 1 | 9.9 | 4000 | 8.1 | 10 | 0 | 9.8 |
| T87 | 2000 | 6.1 | 3364 | 0.0625 | 9.2 | 1000 | 3.9 | 6.1 | −20 | 9.8 |
| T88 | 16000 | 9.8 | 16000 | 0.0625 | 9.9 | 16000 | 9.6 | 5.6 | 20 | 10 |

| | Adjustment | | | | | | |
|---|---|---|---|---|---|---|---|
| | Component 1 | | Component 2 | | Component 3 | | |
| | LB | UB | LB | UB | LB | UB | Rank |
| T01 | 1827 | 8365 | 6007 | 6007 | 9155 | 9155 | 7.8 |
| T02 | 259.5 | 4778.5 | 6211 | 6211 | . | . | 7.3 |
| T22 | 5199 | 5199 | 7135 | 11367 | . | . | 9.2 |
| T35 | 4077 | 7467 | 6777 | 8077 | . | . | . |
| T66 | 14503 | 14963 | . | . | . | . | 8.4 |
| T70 | 14121 | 14253 | . | . | . | . | . |
| T71 | 5513 | 6763 | . | . | . | . | 6.2 |
| T72 | 14253 | 14689 | . | . | . | . | 8.3 |
| T73 | 6375 | 6375 | . | . | . | . | 8.7 |
| T76 | 4701 | 5681 | . | . | . | . | 8.3 |
| T77 | 9515 | 19965 | . | . | . | . | 9.6 |
| T78 | 5931 | 5931 | . | . | . | . | 7.4 |
| T79 | 12382 | 12706 | . | . | . | . | 9.6 |
| T81 | 7609 | 7609 | 8731 | 8731 | . | . | 9.1 |
| T82 | 9393 | 10733 | . | . | . | . | 9.1 |
| T83 | 24418 | 24630 | 14830 | 14830 | . | . | 8.1 |
| T84 | 7545 | 9723 | 9977 | 11061 | . | . | 9.3 |
| T85 | 10193 | 18289 | . | . | . | . | 5.9 |
| T86 | 1891 | 3073 | 3859 | 6059 | 6923 | 16019 | 10 |
| T87 | 1005 | 1183 | 2457 | 2457 | . | . | 9.2 |
| T88 | 15269 | 16145 | 12637 | 19845 | . | . | 9.7 |

CF: center frequency; BW: bandwidth; WN: White Noise; TNR: Tone in Noise Ratio; LB: lower band; UB: upper band

The invention claimed is:

1. A method for matching tinnitus in a subject, comprising:

applying a plurality of sounds to the subject, via an audio interface of a computing apparatus, the plurality of sounds comprising a plurality of first sounds and further comprising a plurality of second sounds;

controlling, by the computing apparatus, display of an input interface for tinnitus matching including a representation of frequency, a representation of a lower cutoff frequency, a representation of an upper cut-off frequency, and a volume control;

receiving, by the computing apparatus, adjustment of the volume control from the subject, wherein adjustment of the volume control provides adjustment of a perceived loudness of sound that corresponds to a loudness of tinnitus of the subject;

adjusting, by the computing apparatus, a frequency of applied sound;

receiving, by the computing apparatus, adjustment of the representation of the lower cutoff frequency and adjustment of the representation of the upper cutoff frequency from the subject, wherein adjustment of the representation of the lower cutoff frequency and adjustment of the representation of the upper cutoff frequency provides perceived cutoff frequencies of a band-pass noise that corresponds to the tinnitus of the subject, wherein the perceived cutoff frequencies correspond to an upper cutoff frequency of the tinnitus of the subject and to a lower cutoff frequency of the tinnitus of the subject;

determining, by the computing apparatus, a center frequency and a frequency bandwidth based on the perceived cutoff frequencies, wherein the center frequency relates to an average of the perceived upper cutoff frequency and the perceived lower cutoff frequency, and wherein the frequency bandwidth is based on a difference between the upper cutoff frequency and the lower cutoff frequency;

generating, by the computing apparatus, a second sound that matches the tinnitus of the subject based on the perceived loudness, the center frequency and the frequency bandwidth, wherein the second sound includes a first sound component that matches a first perceived component of the tinnitus of the subject based on the perceived loudness, the center frequency and the frequency bandwidth, wherein the second sound also includes at least one additional sound component corresponding to an additional perceived component of the tinnitus of the subject, wherein the at least one additional sound component is generated including a differing value from the first sound component for at least one of loudness, center frequency and frequency bandwidth, and wherein a mixed sound is generated based on the first sound component and the at least one additional sound component;

receiving, by the computing apparatus, a likeness score for the second sound, wherein the likeness score corresponds to a similarity of the second sound to the tinnitus of the subject; and selecting, by the computing apparatus, the second sound to suppress tinnitus of the subject based on the likeness score matching a threshold or exceeding a threshold.

2. The method of claim 1, wherein the plurality of the first sounds comprises a single frequency component and the plurality of the second sounds comprises multiple frequency components.

3. The method of claim 1, wherein the plurality of first sounds comprises multiple frequency components and the plurality of second sounds comprises multiple frequency components.

4. The method of claim 1, wherein the plurality of first sounds comprises a harmonic and the plurality of second sounds comprises multiple frequency components.

5. A method for matching tinnitus in a subject, comprising:

applying, by an audio interface module of a computing apparatus, a sound to a subject via an audio interface associated with the computing apparatus;

controlling, by the computing apparatus, display of an input interface for tinnitus matching including a representation of frequency, a representation of a lower cut-off frequency, a representation of an upper cut-off frequency, and a volume control;

receiving, by the computing apparatus, adjustment of the volume control from the subject, wherein adjustment of the volume control provides adjustment of a perceived loudness of the sound that corresponds to a loudness of the tinnitus of the subject;

adjusting, by the computing apparatus, a frequency of the sound;

receiving, by the computing apparatus, adjustment of the representation of the lower cut-off frequency and adjustment of the representation of the upper cut-off frequency from the subject, wherein adjustment of the representation of the lower cut-off frequency and adjustment of the representation of the upper cut-off frequency provides perceived cut-off frequencies of a band-pass noise that corresponds to the tinnitus of the subject, wherein the perceived cut-off frequencies correspond to an upper cut-off frequency of the tinnitus of the subject and to a lower cut-off frequency of the tinnitus of the subject;

determining, by the computing apparatus, a center frequency and a frequency bandwidth based on the perceived cut-off frequencies, wherein the center frequency relates to an average of the perceived upper cut-off frequency and the perceived lower cut-off frequency, and wherein the frequency bandwidth is based on a difference between the upper cut-off frequency and the lower cut-off frequency;

generating, by the computing apparatus, a second sound that matches the tinnitus of the subject based on the perceived loudness, the center frequency and the frequency bandwidth, wherein the second sound includes a first sound component that matches a first perceived component of the tinnitus of the subject based on the perceived loudness, the center frequency and the frequency bandwidth, wherein the second sound also includes at least one additional sound component corresponding to an additional perceived component of the tinnitus of the subject, wherein the at least one additional sound component is generated including a differing value from the first sound component for at least one of loudness, center frequency and frequency bandwidth, and wherein a mixed sound is generated based on the first sound component and the at least one additional sound component;

receiving, by the computing apparatus, a likeness score for the second sound, wherein the likeness score corresponds to a similarity of the second sound to the tinnitus of the subject; and selecting, by the computing apparatus, the second sound to suppress tinnitus of the subject based on the likeness score matching a threshold or exceeding a threshold.

6. The method of claim 5, wherein the second sound comprises a single frequency component.

7. The method of claim 5, wherein the second sound comprises multiple frequency components.

8. The method of claim 5, wherein the second sound comprises a harmonic.

9. The method of claim 5, wherein generating the second sound includes generating a plurality of second sounds and wherein selecting includes selecting a second sound from the plurality of second sounds to suppress tinnitus of the subject based on the likeness score of the second sound from the plurality of second sounds matching a threshold or exceeding a threshold.

10. The method of claim 5, wherein the representation of the frequency includes a frequency bar, and wherein adjustment of the representation of the upper cut-off frequency and the representation of the lower cut-off frequency includes adjusting a positions of the representations of the upper cut-off frequency and a position of the representation of the lower cut-off frequency relative to the frequency bar.

11. The method of claim 5, wherein generating the second sound comprises:

generating, by the computing apparatus, a first sound component that matches a first perceived component of the tinnitus of the subject based on the perceived loudness, the center frequency and the frequency bandwidth;

generating, by the computing apparatus, one or more additional sound components, wherein the one or more additional sound components corresponds to an additional perceived component of the tinnitus of the subject; and generating, by the computing apparatus, a mixed sound based on the first sound component and based on the one or more additional sound components; and generating, by the computing apparatus, the second sound based on the mixed sound, wherein each sound component comprises a characteristic different from each other sound component and different from the third sound in one or more of the following aspects: a loudness of the sound component, a center frequency of the sound component, and a frequency bandwidth of the sound component.

12. The method of claim 5, further comprising applying, via the audio interface, the second sound to suppress tinnitus of the subject to the subject, thereby suppressing the tinnitus of the subject.

13. The method of claim 5, further comprising generating, by the computing apparatus, the second sound based on matched tinnitus frequency information from one or more reference subjects.

14. An apparatus for matching the tinnitus of a subject, comprising:
an audio interface module configured to apply a plurality of sounds to the subject, the plurality of sounds comprising a plurality of first sounds and further comprising a plurality of second sounds;
an input module configured to receive likeness scores; and
an audio generation module including
a sound generator; and
an analysis module configured to
control display of an input interface for tinnitus matching including a representation of frequency, a representation of a lower cutoff frequency, a representation of an upper cut-off frequency, and a volume control;
receive adjustment of the volume control from the subject, wherein adjustment of the volume control provides adjustment of a perceived loudness of sound that corresponds to a loudness of tinnitus of the subject;
adjust a frequency of applied sound;
receive adjustment of the representation of the lower cutoff frequency and adjustment of the representation of the upper cutoff frequency from the subject, wherein adjustment of the representation of the lower cutoff frequency and adjustment of the representation of the upper cutoff frequency provides perceived cutoff frequencies of a band-pass noise that corresponds to the tinnitus of the subject, wherein the perceived cutoff frequencies correspond to an upper cutoff frequency of the tinnitus of the subject and to a lower cutoff frequency of the tinnitus of the subject;
determine, a center frequency and a frequency bandwidth based on the perceived cutoff frequencies, wherein the center frequency relates to an average of the perceived upper cutoff frequency and the perceived lower cutoff frequency, and wherein the frequency bandwidth is based on a difference between the upper cutoff frequency and the lower cutoff frequency;
generate a second sound that matches the tinnitus of the subject based on the perceived loudness, the center frequency and the frequency bandwidth,
wherein the second sound includes a first sound component that matches a first perceived component of the tinnitus of the subject based on the perceived loudness, the center frequency and the frequency bandwidth,
wherein the second sound also includes at least one additional sound component corresponding to an additional perceived component of the tinnitus of the subject,
wherein the at least one additional sound component is generated including a differing value from the first sound component for at least one of loudness, center frequency and frequency bandwidth, and wherein a mixed sound is generated based on the first sound component and the at least one additional sound component;
receiving a likeness score for the second sound, wherein the likeness score corresponds to a similarity of the second sound to the tinnitus of the subject; and
select the second sound to suppress tinnitus of the subject based on the likeness score matching a threshold or exceeding a threshold.

15. The apparatus of claim 14, wherein the plurality of first sounds comprises a single frequency component and the plurality of second sounds comprises multiple frequency components.

16. The apparatus of claim 14, wherein the plurality of first sounds comprises multiple frequency components and the plurality of second sounds comprises multiple frequency components.

17. The apparatus of claim 14, wherein the audio generation module is further configured to generate the plurality of sounds based on matched tinnitus frequency information from one or more reference subjects.

18. An apparatus for matching the tinnitus of a subject, comprising:
an audio interface module configured to apply a sound to the subject via an audio interface associated with the apparatus;
an input module configured to display an input interface for tinnitus matching including a representation of frequency, a representation of a lower cut-off frequency, a representation of an upper cut-off frequency, and a volume control; and configured to receive, in response to the applying:
a signal indicative of adjustment of the volume control from the subject, wherein adjustment of the volume control provides adjustment of a perceived loudness of the sound that, corresponds to a loudness of the tinnitus of the subject; and
a signal identifying an adjustment of the representation of the lower cut-off frequency and adjustment of the representation of the upper cut-off frequency from the subject, wherein adjustment of the representation of the lower cut-off frequency and adjustment of the representation of the upper cut-off frequency provides perceived cut-off frequencies of a band-pass noise that corresponds to the tinnitus of the subject, wherein the perceived cut-off frequencies correspond to an upper cut-off frequency of the tinnitus of the subject and to a lower cut-off frequency of the tinnitus of the subject;
a memory constructed to store data corresponding to a center frequency and a frequency bandwidth based on the perceived cut-off frequencies, wherein the center frequency relates to an average of the perceived upper cut-off frequency and the perceived lower cut-off frequency, and wherein the frequency bandwidth is based on a difference between the upper cut-off frequency and the lower cut-off frequency; and
an audio generation module comprising:
a sound generator to generate a second sound corresponding to the tinnitus of the subject based on the perceived loudness, the characteristic center frequency and the frequency bandwidth;
wherein the second sound includes a first sound component that matches a first perceived component of the tinnitus of the subject based on the perceived loudness, the center frequency and the frequency bandwidth,
wherein the second sound also includes at least one additional sound component corresponding to an additional perceived component of the tinnitus of the subject,
wherein the at least one additional sound component is generated including a differing value from the first sound component for at least one of loudness, center frequency and frequency bandwidth, and wherein a mixed sound is generated based on the first sound component and the at least one additional sound component;

wherein the input module is further configured to receive a first likeness score associated with the second sound, wherein the likeness score corresponds to the similarity of the second sound to the tinnitus of the subject, and wherein the audio generation module is further configured to:

select the second sound for applying to the subject if the first likeness score matches or exceeds a threshold; and reject the second sound if the likeness score does not match or exceed the threshold;

wherein at least one of the audio interface module, the input module, and the audio generation module comprises one or more of the memory and a processing device.

* * * * *